(12) United States Patent
Mohapatra

(10) Patent No.: US 8,623,835 B2
(45) Date of Patent: Jan. 7, 2014

(54) MATERIALS AND METHODS FOR TREATMENT OF RESPIRATORY ALLERGIC DISEASES

(75) Inventor: Shyam S. Mohapatra, Tampa, FL (US)

(73) Assignee: University of South Florida, Tampa, FL (US)

( * ) Notice: Subject to any disclaimer, the term of this patent is extended or adjusted under 35 U.S.C. 154(b) by 1296 days.

(21) Appl. No.: 11/936,491

(22) Filed: Nov. 7, 2007

(65) Prior Publication Data

US 2008/0070858 A1    Mar. 20, 2008

Related U.S. Application Data

(62) Division of application No. 10/526,584, filed as application No. PCT/US03/28056 on Sep. 8, 2003, now Pat. No. 7,655,772.

(60) Provisional application No. 60/319,529, filed on Sep. 6, 2002.

(51) Int. Cl.
*A61K 48/00*    (2006.01)

(52) U.S. Cl.
USPC ..................................... 514/44 R; 435/320.1

(58) Field of Classification Search
None
See application file for complete search history.

(56) References Cited

U.S. PATENT DOCUMENTS

| | | |
|---|---|---|
| 4,957,735 A | 9/1990 | Huang |
| 5,013,556 A | 5/1991 | Woodle et al. |
| 5,043,164 A | 8/1991 | Huang et al. |
| 5,180,818 A | 1/1993 | Cech et al. |
| 5,595,756 A | 1/1997 | Bally et al. |
| 5,646,032 A | 7/1997 | ter Meulen et al. |
| 5,686,101 A | 11/1997 | Tagawa et al. |
| 5,691,310 A * | 11/1997 | Vesely ............................ 514/12 |
| 5,705,187 A | 1/1998 | Unger |
| 5,817,856 A | 10/1998 | Tirosh et al. |
| 5,820,873 A | 10/1998 | Choi et al. |
| 5,840,341 A | 11/1998 | Watts et al. |
| 6,013,630 A | 1/2000 | Shimkets |
| 6,028,055 A | 2/2000 | Lowe et al. |
| 6,184,037 B1 | 2/2001 | Rolland et al. |
| 6,528,245 B2 | 3/2003 | Sanchez-Ramos et al. |
| 6,943,147 B2 | 9/2005 | Vesely |
| 7,022,828 B2 | 4/2006 | McSwiggen |
| 7,354,908 B2 | 4/2008 | Mohapatra et al. |
| 7,488,713 B2 | 2/2009 | Vesely |
| 7,595,303 B1 | 9/2009 | Mohapatra et al. |
| 7,825,092 B2 | 11/2010 | Vesely |
| 7,846,900 B2 | 12/2010 | Vesely |
| 8,071,560 B2 | 12/2011 | Mohapatra et al. |
| 8,148,114 B2 | 4/2012 | Mohapatra |
| 2001/0027181 A1 | 10/2001 | Kitakaze et al. |
| 2002/0146821 A1 | 10/2002 | Sanchez-Ramos et al. |
| 2002/0193579 A1 | 12/2002 | Usman et al. |
| 2003/0069186 A1 | 4/2003 | Burnett et al. |
| 2003/0073628 A1 | 4/2003 | Shailubhai et al. |
| 2003/0138793 A1 | 7/2003 | Su et al. |
| 2003/0147943 A1 | 8/2003 | Luo et al. |
| 2003/0198640 A1 | 10/2003 | Yu et al. |
| 2003/0204063 A1 | 10/2003 | Gravel et al. |
| 2004/0002458 A1 | 1/2004 | Seilhamer et al. |
| 2004/0067889 A1 | 4/2004 | Belenky et al. |
| 2004/0138134 A1 | 7/2004 | Golembo et al. |
| 2004/0146549 A1 | 7/2004 | Ben-Sasson et al. |
| 2004/0171550 A1 | 9/2004 | Backstrom et al. |
| 2004/0203081 A1 | 10/2004 | James et al. |
| 2004/0213782 A1 | 10/2004 | Wax et al. |
| 2004/0224903 A1 | 11/2004 | Berry et al. |
| 2004/0266673 A1 | 12/2004 | Bakis et al. |
| 2005/0008617 A1 | 1/2005 | Chen et al. |
| 2005/0014287 A1 | 1/2005 | Friese et al. |
| 2005/0014289 A1 | 1/2005 | Parsons et al. |
| 2005/0209139 A1 | 9/2005 | Vesely |
| 2005/0266093 A1 | 12/2005 | Mohapatra |
| 2005/0272650 A1 | 12/2005 | Mohapatra |
| 2006/0014689 A1 | 1/2006 | Vesely |
| 2006/0110359 A1 | 5/2006 | Sanchez-Ramos et al. |
| 2007/0036867 A1 | 2/2007 | Mohapatra et al. |
| 2007/0116767 A1 | 5/2007 | Mohapatra |
| 2007/0178075 A1 | 8/2007 | Chaudhry et al. |

(Continued)

FOREIGN PATENT DOCUMENTS

WO    WO 99/32619 A1    7/1999
WO    WO 00/71576 A2    11/2000

(Continued)

OTHER PUBLICATIONS

Mizuguchi et al. Clin Exp Allergy 2000;300:439-444.*
Louzier et al. Hum Gene Ther 2001;12:503-13.*
Hulks, Brit Med J 1989;299:1081-2.*
Hulks, Brit Med J 1992;304:1156.*
Schwarze et al. J Clin Invest 1997;99:226-33.*
Schipper, N.G.M. et al. "Chitosans as absorption enhancers for poorly absorbable drugs. 1: Influence of molecular weight and degree of acetylation on drug transport across human intestinal epithelial (Caco-2) cells" *Pharm. Res.*, 13(11):1686-1692.
Abbey, S. and Potter, L. "Lysophosphatidic acid inhibits C-type natriuretic peptide activation of guanylyl cyclase-B" *Endocrinology*, 2003, 144:240-246.
Angus, R.M. et al. "Effect of inhaled atrial natriuretic peptide on methecholine induced bronchoconstriction in asthma" *Clin Exp Allergy* 1994, 24:784-788.

(Continued)

*Primary Examiner* — Janice Li
(74) *Attorney, Agent, or Firm* — Saliwanchik, Lloyd & Eisenschenk

(57) ABSTRACT

The present invention pertains to a method for treatment of allergic diseases by administering a natriuretic hormone peptide (NHP), or a nucleic acid sequence encoding NHP, to a patient in need thereof. In another aspect, the present invention concerns an expression vector comprising a nucleic acid sequence encoding NHP. In another aspect, the present invention concerns a host cell genetically modified with a nucleic acid sequence encoding NHP. In another aspect, the present invention concerns a pharmaceutical composition comprising NHP or a nucleic acid sequence encoding NHP and a pharmaceutically acceptable carrier. In another aspect, the present invention pertains to novel fragments of atrial natriuretic peptide (ANP) exhibiting bronchodilatory and anti-inflammatory activity, and isolated nucleic acid sequences encoding the fragments.

24 Claims, 8 Drawing Sheets

(56) References Cited

U.S. PATENT DOCUMENTS

| | | | |
|---|---|---|---|
| 2007/0265204 | A1 | 11/2007 | Mohapatra et al. |
| 2008/0039394 | A1 | 2/2008 | Vesely |
| 2008/0214437 | A1 | 9/2008 | Mohapatra et al. |
| 2009/0062206 | A1 | 3/2009 | Vesely |
| 2009/0170196 | A1 | 7/2009 | Vesely |
| 2009/0176706 | A1 | 7/2009 | Mohapatra |
| 2009/0280143 | A1 | 11/2009 | Mohapatra et al. |
| 2010/0254973 | A1 | 10/2010 | Mohapatra et al. |
| 2010/0260725 | A1 | 10/2010 | Mohapatra et al. |
| 2011/0034386 | A1 | 2/2011 | Vesely |
| 2011/0039777 | A1 | 2/2011 | Vesely |

FOREIGN PATENT DOCUMENTS

| | | |
|---|---|---|
| WO | WO 01/68836 A3 | 9/2001 |
| WO | WO 01/75164 A3 | 10/2001 |
| WO | WO 01/92513 A1 | 10/2001 |
| WO | WO 2004/011498 A3 | 2/2004 |
| WO | WO 2004/022003 A3 | 3/2004 |
| WO | WO 2004/022579 A3 | 3/2004 |
| WO | WO 2005/094420 A2 | 10/2005 |
| WO | WO 2007/127487 A2 | 11/2007 |
| WO | WO 2008/157834 A1 | 12/2008 |
| WO | WO 2009/042173 A1 | 3/2009 |
| WO | WO 2009/073527 A2 | 6/2009 |

OTHER PUBLICATIONS

Angus, R.M. et al. "Effect of inhaled atrial natriuretic peptide and a neutral endopeptidase inhibitor on histamine-induced bronchoconstriction" *Am. J. Respir. Crit. Care Med.*, 1995, 151:2003-2005.

Bliss, D. et al. "Expression of the atrial natriuretic factor gene in small cell lung cancer turmors and tumor cell lines" *J Natl Can Inst*, 1990, 82:305-310.

Boiteau, R. et al. "Increase in atrial natriuretic factor (ANF) in acute severe asthma (ASA)" *Am Rev Res Dis.*, 1988, 137:A484.

Chanez, P. et al. "Atrial natriuretic factor (ANF) is a potent bronchodilator in asthma" *J. Allergy Clin. Immunol.*, 1990, 86:321-324.

Chen, S. et al. "1,25 dihydroxyvitamin D amplifies type A natriuretic peptide receptor epxression and activity in target cells" *J. Am. Soc. Nephrol.*, 2005, 16:329-339.

Delporte, C. et al. "Discovery of a potent atrial natriuretic peptide antagonist for ANP$_A$ receptors in the human neuroblatoma NB-OK-1 cell line" *Eur. J. Pharmacol.*, 1992, 224(2-3):183-188.

Drewett, J.G. and Garbers, D.L. "The family of guanylyl cyclase receptors and their ligands" *Endocrine Reviews*, 1994, 15(2):135-162.

El-Ayoubi, R. et al. "Urinary repsonses to acute moxonidine are inhibited by natriuretic peptide receptor antagonist" *Br. J. Pharmacol.*, 2005, 145:50-56.

Ernst, P. "Review article: the role of inflammation in the pathogenesis of gastric cancer" *Aliment Pharmacol Ther.*, 1999, 13(1):13-18.

Fonarow, G.C. et al. "Combining natriuretic peptides and necrosis markers in determining progonisis in heart failure" *Rev. Cardiovasc. Med.*, 2003, 4(suppl 4):S20-S28.

Fujiseki, Y. et al. "Natriuretic peptide receptors, NPR-A and NPR-B, in cultured rabbit retinal pigment epithelium cells" *Jpn. J. Pharmacol.*, 1999, 79(3):359-368.

Fürst, R. et al. "Atrial natriuretic peptide induces mitogen-activated protein kinase phosphatase-1 in human endothelial cells via Rac1 and NAD(P)H oxidase/Nox2-activation" *Circ. Res.*, 2005, 96:43-53.

Gower. W.R. et al. "Regulation of atrial natriuretic peptide secretion by cholinergic and PACAP neurons of the gastric antrum" *Am. J. Physiol. Gastrointest. Liver Physiol.*, 2003, 284:G68-G74.

Greenberg, B.D. et al. "Nucleotide sequence of the gene encoding human atrial natriuretic factor precursor" *Nature*, 1984, 312(5995):656-658.

Greten, F.R. et al. "IKKβ links inflammation and tumorigenesis in a mouse model of colitis-associated cancer" *Cell*, 2004, 118:285-296.

Hamet, P. and Tremblay, J. "Aspects physiologiques et physiopathoiogiques du facteur natriuretique auriculaire" *Nephrologie*, 1987, 8:7-12, abstract.

Hulks, G. et al. "Effect of atrial natriuretic factor on bronchomotor tone in the normal human airway" *Clin Sci* 1990;79:51-55.

Hulks, G. and Thomson, N.C. "High dose inhaled atrial natriuretic peptide is a bronchodilator in asthmatic subjects" *Eur. Respir. J.*, 1994, 7:1593-1597.

Hulks, G. and Thomson, N.C. "Inhaled atrial natriuretic peptide and asthmatic airways" *Br. Med J*, 1992, 304:1156.

Ishii, Y. et al. "Effects of atrial natriuretic peptide on Type II alveolar epithelial cells of the rat lung. Autoradiographic and morphometric studies" *J Anat.*, 1989, 166:85-95.

Izumi, T. et al. "Blockade of the natriuretic peptide receptor guanylyl cyclase-A inhibits NF-κB activation and alleviates myocardial ischemia/reperfusion injury" *J Clin Invest* 2001, 108:203-213.

Jin, H. et al. "Novel analog of atrial natriuretic peptide selective for receptor-A produces increased diuresis and natriuresis in rats" *J. Clin. Invest.*, 1996, 98:969-976.

Kanwal, S. et al. "Intracellular fragments of the natriuretic peptide receptor-C (NPR-C) attenuate dopamine efflux" *Endocrinology*, 1999. 140(3):1118-1124.

Kelly, R. and Struthers, A. "Are natriuretic peptides clinically useful as markers of heart failure?" *Ann. Clin. Biochem.*, 2001, 38:94-102.

Khurana, M.L. and Pandey, K.N. "Receptor-mediated stimulatory effect of atrial natriuretic factor, brain natriuretic peptide, and C-type natriuretic peptide on testosterone production in purified mouse Leydig cells: Activation of cholesterol side-chain cleavage enzyme" *Endocrinology*, 1993, 133:2141-2149.

Kiemer, A. and Vollmar, A. "Autocrine regulation of inducible nitric-oxide synthase in macrophages by atrial natriuretic peptide" *J Biol Chem*, 1998, 273:13444-13451.

Kiemer, A. et al. "cGMP-mediated inhibition of TNF-α production by the atrial natriuretic peptide in murine macrophages" *J Immunol*, 2000, 165:175-181.

Kumar, R. et al. "Expression of guanylyl cyclase-A/atrial natriuretic peptide receptor blocks the activation of protein kinse C in vascular smooth muscle cells" *Hypertension*, 1997, 29(part 2):414-421.

Kumar, M. et al. "Intranasal IFN-γ gene transfer protects BALB/c mice against respiratory syncytial virus infection" *Vaccine* 1999; 18:558-567.

Kumar, M et al. "Atrial natriuretic peptide gene transfer by means of intranasal administration attenuates airway reactivity in a mouse model of allergic sensitization" *J Allergy Clin Immunol.*, 2002, 110:879-882.

Kurihara, M. et al. "Lower number of atrial natriuretic peptide receptors in thymocytes and spleen cells of spontaneously hypertensive rats" *Biochem Biophys Res Commun* 1987, 149:1132-1140.

Liang, F. et al. "Sp1 dependence of natriuretic peptide receptor A gene transcription in rat aortic smooth muscle cell" *Endocrinology*, 1999, 140(4):1695-1701.

Louzier, V. et al. "Adenovirus-mediated atrial natriuretic protein expression in the lung protects rats from hypoxia-induced pulmonary hypertension" *Hum Gene Ther*, 2001, 12:503-513.

Maisel, A.S. et al. "Cardiac natriuretic peptides: A proteomic window to cardiac function and clinical management" *Rev. Cardiovasc. Med.*, 2003, 4(suppl 4):S3-S12.

Martin, J. et al. "Modulation by biologic response modifiers of hepatitis C virus antigen-independent cytokine secretion in blood mononuclear cells" *Cytokine*, 1999, 11:267-270.

Matanić, D. et al. "Cytokines in patients with lung cancer" *Scand J Immunol*, 2003, 57:173-178.

Matsukawa, N. et al. "The natriuretic peptide clearance receptor locally modulates the physiological effects of the natriuretic peptide system" *Proc. Natl. Acad. Sci. USA*, 1999, 96:7403-7408.

Matsuse, H. et al. "Recurrent repsiratory syncytial virus infections in allergen-sensitized mice lead to persistent airway inflammation and hyperresponsiveness" *J Immunol*, 2000, 164:6583-6592.

Mohapatra, S. et al. "Natriuretic peptides and genesis of asthma: An emerging paradigm?" *J Allergy Clin Immunol*, 2004, 114:520-526.

Motohashi, S. et al. "Preserved IFN-α production of circulating Vα24 NKT cells in primary lung cancer patients" *Int J Cancer* 2002, 102:159-165.

(56) References Cited

OTHER PUBLICATIONS

Mueller, C. and Buser, P. "B-type natriuretic peptide (BNP): can it improve our management of patients with congestive heart failure?" *Swiss Med Wkly*, 2002, 132:618-622.

Nakagawa, K. et al. "Plasma concentrations of atrial and brain natriuretic peptides in a case with hypertensive encephalopathy" *Neurol. Res.*, 2002, 24:627-630.

Nazario, B. et al. "Atrial and brain natriuretic peptides stimulate the production and secretion of C-type natriuretic peptide from bovine aortic endothelial cells" *J. Clin. Invest.*, 1995, 95:1151-1157.

Needleman, P. and Greenwald, J.E. "Atriopeptin: a cardiac hormone intimately involved in fluid, electrolyte, and blood-pressure homeostasis" *N Engl J Med*, 1986, 314:828-834.

Ohbayashi, H. et al. "Compared effects of natriuretic peptides on ovalbumin-induced asthmatic model" *Eur. J. Pharmac.*, 1998, 346:55-64.

Ohsaki, Y. et al. "Human small cell lung cancer cell lines express functional atrial natriuretic peptide receptors" *Cancer Res*, 1993, 53:3165-3171.

Ohsaki, Y. et al. "Human small cell lung cancer cells produce brain natriuretic peptide" *Oncology*, 1999, 56:155-159.

Ohyama, Y. et al. "Stable expression of natriuretic peptide receptors: Effects of HS-142-1, a non-peptide ANP antagonist" *Biochem. Biophys. Res. Commun.*, 1992, 189(1):336-342.

Pandey, K.N. et al. "Natriuretic peptide receptor-A negatively regulates mitogen-activated protein kinase and proliferation of mesangial cells: Role of cGMP-dependent protein kinase" *Biochem. Biophys. Res. Commun.*, 2000, 271(2):374-379.

Pandey, K.N. et al. "Internalization and trafficking of guanylyl (guanylate) cyclase/natriuretic peptide receptor A is regulated by an acidic tyrosine-based cytoplasmic motif GDAY" *Biochem. J.*, 2005, 388:103-113.

Pandey, K.N. et al. "Ligand-regulated internalization, trafficking, and down-regulation of guanylyl cyclase/atrial natriuretic peptide receptor-A in human embryonic kidney 293 cells" *J. Biol. Chem.*, 2002, 277(7):4618-4627.

Pandey, K.N. et al. "Functional domains and expression of truncated atrial natriuretic peptide receptor-A: The carboxyl-terminal regions direct the receptor internalization and sequestration in COS-7 cells" *Molecular Pharmacology*, 2000, 57:259-267.

Pandey, K.N. "Dynamics of internalization and sequestration of guanylyl cyclase/atrial natriuretic peptide receptor-A" *Can. J. Physiol. Pharmacol.*, 2001, 79(8):631-639.

Pandey, K N. "Intracellular trafficking and metabolic turnover of ligand-bound guanylyl cyclase/atrial natriuretic peptide receptor-A into subcellular compartments" *Mol. Cell. Biochem.*, 2002, 230(1-2):61-72.

Pikarsky, E. et al. "NF-κB functions as a tumour promoter in inflammation-associated cancer" *Nature*, 2004, 431:461-466.

Prins, B.A. et al. "Atrial natriuretic peptide inhibits mitogen-activated protein kinase through the clearance receptor" *J. Biol. Chem.*, 1996, 271(24):14156-14162.

Rouleau, N. et al. "Development of a Non-radioactive Homogenous HTS Platform to Measure the Activity of Guanylate Cyclase", Poster #P10144, Presented at 10th Annual SBS Conference and Exhibition, Orlando, FL, Sep. 11-15, 1004, Perkinelmer Biosignal Inc., Canada.

Roy, K. et al. "Oral gene delivery with chitosan-DNA nanoparticles generates immunologic protection in a murine model of peanut allergy" *Nat Med*, 1999, 5:387-391.

Rutherford, R. et al. "Identification of renal natriuretic peptide receptor subpopulations by use of the non-peptide antagonist, HS-142-1" *Br. J. Pharmacol.*, 1994, 113:931-939.

Seidman, G.E. et al. "The structure of rat preproatrial natriuretic factor as defined by a complementary DNA clone" *Science*, 1984, 25:324-326.

Seidman, C.E. et al. "Nucleotide sequences of the human and mouse atrial natriuretic factor genes" *Science*, 1984, 226:1206-1209.

Sekiguchi, T. et al. "Molecular cloning of natriuretic peptide receptor A from bullfrog (*Rana catesbeiana*) brain and its functional expression" *Gene*, 2001, 273:251-257.

Sharma, G.D. et al. "Expression of atrial natriuretic peptide receptor-A antagonizes the mitogen-activated protein kinases (Erk2 and P38$^{MAPK}$) in cultured human vascular smooth muscle cells" *Mol. Cell. Biochem.*, 2002, 233(1-2):pp. 165-173.

Shi, S-J. et al. "Natriuretic peptide receptor A mediates renal sodium excretory responses to blood volume expansion" *Am. J. Physiol. Renal Physiol.*, 2003, 285:F694-F702.

Shimizu, K. et al. "Ectopic atrial natriuretic peptide production in small cell lung cancer with the syndrome of inappropriate antidiuretic hormone secretion" *Cancer* 1991, 68:2284-2288.

Silberbach, M. and Roberts Jr., C. "Natriuretic peptide signaling molecular and cellular pathways to growth regulation" *Cell Signal*, 2001, 13:221-231.

Simkins, J. "Nesiritide (Natrecor®) for Decompensated CHF" in The University of Montana's School of Pharmacy and Allied Health Sciences Drug Information Service, Apr. 2002, vol. 6 No. 4.

Suenobu, N. et al. "Natriuretic peptides and nitric oxide induce endothelial apoptosis via a cGMP-dependent mechanism" *Arterioscler Thromb Vasc Biol.*, 1999, 19:140-146.

Suric-Lambic, L. et al. "Vasoactive natriuretic peptides and kidney" *Facta Universitatis: Medicine and Biology*, 1998, 5(1):6-11.

True, D. et al. "Comparison of Kinase Assay Technologies for High Throughput Screening" poster presented at Society for Biomolecular Screening (SBS), 8th Annual Conference, Sep. 22-26, 2002.

Vesely, B.A. et al. "Four peptides decrease the number of human pancreatic adenocarcinoma cells" *Eur. J. Clin. Invest.*, 2003, 33:998-1005.

Vesely, D.L. "Atrial natriuretic peptides in pathophysiological diseases" *Cardiovascular Res.*, 51:647-658.

Wang, W. et al. "AlbuBNP, a recombinant B-type natriuretic peptide and human serum albumin fusion hormone, as a long-tears therapy of congestive heart failure" *Pharm. Res.*, 2004, 21(11):2105-2111.

Winquist, R. et al. "Atrial natriuretic factor elicits an endothelium-independent relaxation and activates particulate guanylate cyclase in vascular smooth muscle" *Proc. Natl. Acad. Sci. USA*, 1984, 81:7661-7664.

Chen, X. et al. "Human bone marrow stromal cell cultures" *J Neurosci Res.*, 2002, 69:687-691.

Chen, X. et al. "Ischemic rat brain extracts induce human marrow stromal cell growth factor production" *Neuropathology*, 2002, 22:275-279.

Chen, J. et al. "Therapeutic benefit of intravenous administration of bone marrow stromal cells after cerebral ischemia in rats" *Stroke*, 2001, 32:1005-1011.

Chen, J. et al. "Therapeutic benefit of intracerebral transplantation of bone marrow stromal cells after cerebral ischemia in rats" *J. Neurological Sci.*, 2001, 189:49-57.

Chopp, M. et al. "Spinal cord injury in rat: treatment with bone marrow stromal cell transplantation" *Neuroreport*, 2000, 11:3001-3005.

Doczi, T.P. et al. "Atrial natriuretic peptide (ANP) attenuates brain oedema accompanying experimental subarachnoid haemorrhage" *Acta Neurochir (Wien)*, 1995, 132:87-91.

Jensen, K.T. et al. "A new, fast and reliable radioimmunossay of brain natriuretic peptide in human plasma. Reference values in healthy subjects and in patients with different diseases" *Scand J Clin Lab Invest*, 1997, 57:529-540.

Kaneko, T. et al. "C-type natriuretic peptide (CNP) is the major natriuretic peptide in human cerebrospinal fluid" *Brain Res*, 1993, 612:104-109.

Kojima, M. et al. "Cloning and sequence analysis of cDNA encoding a precursor for rat brain natriuretic peptide" *Biochem. Biophys. Res. Commun.*, 1989, 159(3):1420-1426.

Li, Y. et al. "Intrastriatal transplantation of bone marrow nonhematopoietic cells improves functional recovery after stroke in adult mice" *Journal of Cerebral Blood Flow & Metabolism*, 2000, 20:1311-1319.

Li, Y. et al. "Human marrow stromal cell therapy for stroke in rat: Neutotrophins and functional recovery" *Neurology*, 2002, 59:514-523.

Lu, D. et al. "Adult bone marrow stromal cells administered intravenously to rats after traumatic brain injury migrate into brain and improve neurological outcome" *Neuroreport*, 2001, 12:559-563.

(56) References Cited

OTHER PUBLICATIONS

Mahmood, A. et al. "Treatment of traumatic brain injury in female rats with intravenous administration of bone marrow stromal cells" *Neurosurgery*, 2001, 49:1196-1204.

Mahmood, A. et al. "Intracranial bone marrow transplantation after traumatic brain injury improving functional outcome in adult rats" *Journal of Neurosurgery*, 2001, 94:589-595.

Mahmood, A. et al. "Intracerebral transplantation of marrow stromal cells cultured with neurotrophic factors promotes functional recovery in adult rats subjected to traumatic brain injury" *J Neurotrauma*, 2002, 19:1609-1617.

Nakao, N. et al. "Effect of atrial natriuretic peptide on ischemic brain edema: Changes in brain water and electrolytes" *Neurosurgery*, 1990, 27:39-44.

Naruse, S. et al. "Effects of atrial natriuretic peptide on brain oedema: The change of water, sodium, and potassium contents in the brain" *Acta Neurochir Suppl (Wien)*, 1990, 51:118-121.

Nocera, R. et al. "Novel strategies of neuroprotection against pathologic consequences of stroke in the aged brain" *Society for Neurosci. Abstracts*, 2001, 27(2):2302, Meeting date Nov. 10-15, 2001.

Ogawa, Y. et al. "Molecular cloning of the complementary DNA and gene that encode mouse brain natriuretic peptide and generation of transgenic mice that overexpress the brain natriuretic peptide gene" *J. Clin. Invest.*, 1994, 93(5):1911-1921.

Porter, J.G. et al. "Cloning of a cDNA encoding porcine brain natriuretic peptide" *J. Biol. Chem.*, 1989, 264(12):6689-6692.

Quan, H. et al. "Inducible regulation of human brain natriuretic peptide promoter in transgenic mice" *Am. J. Physiol. Heart Circ. Physiol.*, 2001, 280:H368-H376.

Roy. R.N. and Flynn, T.G. "Organization of the gene for iso-rANP, a rat B-type natriuretic peptide" *Biochem. Biophys. Res. Commun.*, 1990, 171(1):416-423.

Sanchez-Ramos, J.R. "Neural cells derived from adult bone marrow and umbilical cord blood" *J. Neurosci. Res.*, 2002, 69:880-893.

Seilhamer, J.J. et al. "Human and canine gene homologs of porcine brain natriuretic peptide" *Biochem. Biophys. Res. Commun.*, 1989, 165(2):650-658.

Song, S. et al. "Nerve growth factor and retinoic acid induce development of neuronal cells from bone marrow stromal cells of both young and old mice" *Society for Neurosci. Abstracts*, 2001, 27(1):940, Meeting date Nov. 10-15, 2001.

Song, S. et al. "Expression of brain natriuretic peptide by human bone marrow stromal cells" *Society for Neurosci. Abstracts*, 2002, Abstract No. 824.3, Meeting date Nov. 2-7, 2002.

Song, S. and Sanchez-Ramos, J. "Preparation of Neural Progenitors from Bone Marrow and Umbilical Cord Blood" in Protocols for Neural Stem Cell Methods, Zigova, T. et al., Eds., 2002, pp. 79-88.

Song, S. et al. "Expression of brain natriuretic peptide by human bone marrow stromal cells" *Experimental Neurology*, 2004, 185:191-197.

Steinhelper, M.E. "Structure, expression, and genomic mapping of the mouse natriuretic peptide type-B gene" *Circ. Res.*, 1993, 72(5):984-992.

Sudoh, T. et al. "Brain natriuretic peptide-32: N-terminal six amino acid extended form of brain natriuretic peptide identified in porcine brain" *Biochem Biophys Res Commun*, 1988, 155:726-732.

Vlasuk, G.P. et al. "Structure and analysis of the bovine atrial natriuretic peptide precursor gene" *Biochem. Biophys. Res. Commun.*, 1986, 136(1):396-403.

Zivin, R.A. et al. "Molecular cloning and characterization of DNA sequences encoding rat and human atrial natriuretic actors" *Proc. Natl. Acad. Sci. USA*, 1984, 81(20):6325-6329.

Lin et al., "Human Atrial Natriuretic Peptide Gene Delivery Reduces Blood Pressure in Hypertensive Rats" *Hypertension*, 1995, pp. 847-853, vol. 26.

Lin et al., "Atrial Natriuretic Peptide Gene Delivery Attenuates Hypertension, Cardiac Hypertrophy, and Renal Injury in Salt-Sensitive Rats" *Human Gene Therapy*, Jul. 1, 1998, pp. 1429-1438, vol. 9.

"Atrial natriuretic factor receptor A", MeSH results, accessed http://www.ncbi.nlm.nih.gov/mesh on Dec. 3, 2009, pp. 1-2.

*Peptide hormones* from http://web.indstate.edu/thcme/mwking/peptide-hormones.html, pp. 1-15.

Allen, T.M. et al. "Large unilamellar liposomes with low uptake into the reticuloendothelial system" *FEBS Letters*, 1987, 223:42-46.

Arenberg, D. "Chemokines in the Biology of Lung Cancer" *Journal of Thoracic Oncology*, 2006, 1(4):287-288.

Ashworth, T. et al. "Cutting Edge: TFII-I Controls B Cell Proliferation via Regulating NF-κB" *Journal of Immunology*, 2007, 178:2631-2635.

Baldini, P.M. et al. "Decrease of polyamine levels and enhancement of transglutaminase activity in selective reductionof B16-F10 melanoma cell proliferation induced by atrial natriuretic peptide" *Melanoma Research*, 2006, 16:501-507.

Bryan, P.M. et al. "The Atrial Natriuretic Peptide Receptor (NPR-A/GC-1) is Dephosphorylated by Distinct Microcystin-sensitive and Magnesium-dependent Protein Phosphatase" *J. Biol. Chem.*, 2002, 277(18):16041-16047.

Cane, A. et al. "The Endogenous Oxindoles 5-Hydroxyoxindole and Isatin Are Antiproliferation and Proapoptotic" *Biochemical and Biophysical Research Communications*, 2000, 276:379-384.

Clark, A.R. "Mechanisms of steroid action and resistance in inflammation: MAP kinase phosphatase 1: a novel mediator of biological effects of glucocorticoids" *Journal of Indocrinology*, 2003, 178:5-12.

Collins, F.S. et al. "Generation and initial analysis of more than 15,000 full-length human and mouse cDNA sequences" *Proc Natl Acad Sci*, 2002:99:16899-16903.

Eichelbaum, E.J. et al. "Cardiac and kidney hormones cure up to 86% of human small-cell lung cancers in mice" *Eur J Clin Invest*, 2008, 38(8):562-570.

Fattal, et al. "Biodegradable polyalkylcyanoacrylate nanoparticles for the delivery of oligonucleotides" *Journal of Controlled Release*, 1998, 53:137-143.

Filomeni, G. et al. "Pro-apoptotic Activity of Novel Isatin-Schiff Base Copper(II) Complexes Depends on Oxidative Stress Induction and Organelle-selective Damage" *Journal of Biological Chemistry*, 2007, 282(16):12010-12021.

Frossmann, W.G. et al. "The renal urodilatin system: clinical implications" *Cardiovascular Research*, 2001, 51:450-462.

Glover, V. et al. "Isatin: Identity with the Purified Endogenous Monamine Oxidase Inhibitor Tirublin" *Journal of Neurochemistry*, 1988, 51(2):656-659.

Helene, C. et al. "Control of Gene Expression by Triple Helix-Forming Oligonucleotides: The Antigene Strategy" *Annals of the New York Academy of Sciences*, 1992, 660(1):27-36.

Hellerman, G. et al. "Mechanism of bronchoprotective effects of a novel natriuretic hormone peptide" *Journal of Allergy and Clinical Immunology*, 2004, 113:79-85.

Hirata, Y. "Heterologus Down-Regulation of Vascular Atrial Natriuretic Peptide Receptors by Phorbol Esters" *Biochemical and Biophysical Research Communications*, May 16, 1988, 152(3):1097-1103.

Ho, R.J.Y. et al. "Target-sensitive immunoliposomes: preparation and characterization" *Biochemistry*, 1986, 25:5500-5506.

Ho, R.J.Y. et al. "Interactions of Target-sensitive Immunoliposomes with Herpes Simplex Virus" *The Journal of Biological Chemistry*, 1987, 262(29):13979-13984.

Ho, R.J.Y. et al. "Target-sensitive immunoliposomes as an efficient drug carrier for antiviral activity" *The Journal of Biological Chemistry*, 1987, 262(29):13973-13978.

Howard, K.A. et al."RNA Interference in Vivo and in Vitro Using a Chitosan/siRNA Nanoparticle System" *Molecular Therapy*, 2006, 14(4):476-484.

Karin, M. "Mitogen activated protein kinases as targets for development of novel anti-inflammatory drugs" *Annals of the Rheumatic Diseases*, 2004, 63(Suppl. 2):ii62-ii64.

Katas, H. et al. "Development and characterisation of chitosan nanoparticles for siRNA delivery" *Journal of Controlled Release*, 2006, 115(2):216-225.

Klibanov, A.L. et al. "Amphipathic polyethyleneglycols effectively prolong the circulation time of liposomes" *FEBS Letters*, 1990, 268:235-237.

(56) References Cited

OTHER PUBLICATIONS

Knaapen, A.M. et al. "Inhaled particles and lung cancer. Part A: Mechanisms" *International Journal of Cancer*, 2004, 109:799-809.

Kong, X. et al. "Natriuretic Peptide Receptor A as a Novel Anticancer Agent" *Cancer Research*, Jan. 2008, 68(1):249-256.

Lambert, G. et al. Nanoparticulate systems for the delivery of antisense oligonucleotides *Advanced Drug Delivery Reviews*, Mar. 2001, 47:99-112.

Lenz, A. et al. "Cardiac Hormones Eliminate some Human Squamous Lung Carcinomas in Athymic Mice" *European Journal of Clinical Investigation*, 2010 in press, p. 1-13.

Levin, E.R. et al. "Mechanisms of Disease: Natriuretic Peptides" *New England Journal of Medicine*, 1998, 339:321-328.

Liu, Y. et al. "Discovery of Inhibitors that Elucidate the Role of UCH-L1 Activity in the H1299 Lung Cancer Cell Line" *Chemistry & Biology*, 2003, 10(9):837-846.

Liu, X. et al. "The influence of polymeric properties on chitosan/siRNA nanoparticle formulation and gene silencing" *Biomaterials*, 2007, 28:1280-1288.

Martey, C.A. et al. "Cigarette smoke induces cyclooxygenase-2 and microsomal prostaglandin $E_2$ synthase in human lung fibroblasts: implications for lung inflammation and cancer" *Am J Physiol Lung Cell Mol Physiol*, 2004, 287:L981-991.

Massion P.P. et al. "The molecular basis of lung cancer: molecular abnormalities and therapeutic implications" *Respiratory Research*, 2003, 4(1):12.1-12.15.

Misono, K.S. "Natriuretic peptide receptor: Structure and signaling" *Molecular and Cellular Biochemistiy*, 2002, 230:49-60.

Mohapatra, S.S. et al. "Role of natriuretic peptide signaling in modulating asthma and inflammation" *Can J Physiol Pharmacol*, 2007, 85:754-759.

Morita, R. et al. "Atrial Natriuretic Peptide Polarizes Human Dendritic Cells Toward a Th2-Promoting Phenotype Through Its Receptor Guanylyl Cyclase-Coupled Receptor A1" *The Journal of Immunology*, 2003, 170:5869-5875.

Nafee, N. et al. "Chitosan-coated PLGA nanoparticles for DNA/RNA delivery: effect of the formulation parameters on complexation and transfection of antisense oligonucleotides" *Nanomedicine: Nanotechnology, Biology, and Medicine*, 2007, 3(3):173-183.

Nuglozeh, E. et al. "Gene expression of natriuretic peptide receptors in rats with DOCA-salt hypertension" *Am J Physiol Cell Physiol*, 1997, 273:1427-1434.

Palaparti, A. et al. "Inhibition of atrial natriuretic peptide (ANP) C receptor expression by antisense oligodeoxynucleotides in A10 vascular smoth-muscle cells is associated with attenuation of ANP-C-receptor-mediated inhibition of adenylyl cyclase" *Biochem J*, 2000, 346:313-320.

Pedram, A. et al. "Natriuretic Peptides Inhibit G Protein Activation. Mediation Through Cross-Talk Between Cyclic GMP-Dependent Protein Kinase and Regulators of G Protein-Signaling Proteins" *J. Biol. Chem.*, 2000, 275:7365-7372.

Saccani, A. et al. "p50 Nuclear Factor-κB Overexpression in Tumor-Associated Macrophages Inhibits M1 Inflammatory Responses and Antitumor Resistance" *Cancer Research*, Dec. 2006, 66(23):11432-11440.

Sumpter, W.C. "The Chemistry of Isatin" *Chemical Reviews*, 1944, 34(3):393-434.

Tremblay, J. et al. "Biochemistry and physiology of the natriuretic peptide receptor guanylyl cyclases" *Molecular and Cellular Biochemistry*, 2002, 230:31-47.

Tunny, T.J. et al. "Association of Restriction Fragment Length Polymorphism at the Atrial Natriuretic Peptide Gene Locus with Aldosterone Responsiveness to Angiotensin in Alodsterone-Producing Adenoma" *Biochemical and Biophysical Research Communications*, 1994, 204:1312-1317.

Vellaichamy, E. et al. "Reduced cGMP signaling activates NF-κB in hypertrophied hearts of mice lacking natriuretic peptide receptor-A" *Biochemical and Biophysical Research Communications*, 2005, 324:106-111.

Verma, I.M. et al. "Gene Therapy—promises, problems and prospects" *Nature*, 1997, 389:239-242.

Vesely, D.L. et al. "Atrial natriuretic peptides negatively and positively modulate circulating endothelin in humans" *Metabolism*, 1996, 45:315-319.

Vesely, D.L. et al. "Vessel dilator, long acting natriuretic peptide, and kaliuretic peptide increase circulating prostaglandin $E_2$" *Life Sciences*, 2000, 66:095-913.

Vesely, D.L. et al. "Atrial Natriuretic Hormone, Vessel Dilator, Long-Acting Natriuretic Hormone, and Kaliuretic Hormone Decrease the Circulating Concentrations of CRH, Corticotropin, and Cortisol" *J Clin Endocrinol Metab*, 2001, 86:4244-4249.

Vesely, D.L. et al. "Atrial Natriuretic Hormone, Vessel Dilator, Long Acting Natriuretic Hormone, and Kaliuretic Hormone Decrease Circulating Prolactin Concentrations" *Horm Metab Res*, 2002, 34:245-249.

Vesely, D.L. "Atrial Natriuretic Peptide Prohormone Gene Expression: Hormones and Diseases That Upregulate its Expression" *IUBMB Life*, 2002, 53(3):153-159.

Vesely, D.L. et al. "Four Cardiac Hormones Eliminate up to Two-Thirds of Human Breast Cancers in Athymic Mice" *In Vivo*, 2007, 21:973-978.

Vesely, D.L. et al. "Elimination of Up to 80% of Human Pancreatic Adenocarcinomas in Athymic Mice by Cardiac Hormones" *In Vivo*, 2007, 21:445-452.

Vesely, B.A. et al. "Four peptide hormones decrease the number of human breast adenocarcinoma cells" *European Journal of Clinical Investigation*, 2005, 35:60-69.

Vesely, B.A. et al. "Four Cardiac Hormones Cause Cell Death of Melanoma Cells and Inhibit Their DNA Synthesis" *Am J Med Sci*, 2007, 334(5):342-349.

Vine, K.L. et al. "In vitro cytotoxicity evaluation of some substituted isatin derivatives" *Bioorganic & Medicinal Chemistry*, 2007, 15(2):931-938.

Wang, X. et al. "Modulation of lung inflammation by vessel dilator in a mouse model of allergic asthma" *Respiratory Research*, Jul. 2009. 10(66):1-8.

Wang, X. et al. "Prevention of airway inflammation with topical cream containing imiquimod and small interfering RNA for natriuretic peptide receptor" *Genetic Vaccines and Therapy*, Feb. 2008, 6(7):1-9.

Woodle, M.C. et al. "Sterically stabilized liposomes" *Biochimica et Biophysica Acta: Reviews on Biomembranes*, 1992, 1113:171-199.

Wang, X. et al. "siRNA Targeting the Natriuretic Peptide Receptor-A Prevents Airway Inflammation in a Mouse Model of Allergic Asthma" *Journal of Allergy and Clinical Immunology*, Jan. 2007, 119(1):S131, abstract 515.

Kong, X. et al. "Mice Deficient in Atrial Natriuretic Peptide Receptor A (NPRA) Exhibit Decreased Lung Inflammation: Implication of NPRA Signaling in Asthma Pathogenesis" *Journal of Allergy and Clinical Immunology*, Jan. 2007, 119(1):S127, abstract 501.

Office Action dated Jan. 22, 2013 in U.S. Appl. No. 12/679,630, filed Jun. 28, 2010.

Bradfute, SB et al., "Roles of Sca-1 in hermatopoietic stem/progenitor cell function" 2005, 33:836-843.

Delorme, B and Charbord, P, "Culture and Characterization of Human Bone Marrow Mesenchymal Stem Cells" *Methods in Molecular Medicine*, 2007, 140:67-81.

Hattan, N et al., "Purified cardiomyocytes from bone marrow mesenchymal stem cells produce stable intracardiac grafts in mice" *Cardiovascular Research*, 2005, 65:334-344.

Lu, Y et al., "Human Bone Marrow Mesenchymal Stem Cells Transfected with Human Insulin Genes Can Secrete Insulin Stably" *Annals of Clinical & Laboratory Science*, 2006, 36(2):127-136.

Nadri, S et al., "An efficient method for isolation of murine bone marrow mesenchymal stem cells" *International Journal of Developmental Biology*, 2007, 51:723-729.

Zahabi, A et al., "Expression of Constitutively Active Guanylate Cyclase in Cardiomyocytes Inhibits the Hypertrophic Effects of Isoproternol and Aortic Constriction on Mouse Hearts" *The Journal of Biological Chemistry*, 2003, 278(48):47694-47699.

Office Action dated Apr. 30, 2012 in U.S. Appl. No. 11/998,792, filed Nov. 30, 2007.

(56) References Cited

OTHER PUBLICATIONS

U.S. Appl. No. 13/312,854, filed Dec. 6, 2011, Mohapatra et al.
Angus, R.M. et al. "Bronchodilator, cardiovascular, and cyclic guanylyl monophosphate response to high-dose infused atrial natriuretic peptide in astham" *Am. Rev. Respir. Dis.*, 1993, 147(5):1122-1125, abstract.
Costello, J.M. et al. "A review of the natriuretic hormone system's diagnostic and therapeutic potential in critically ill children" *Pediatr. Crit. Care Med.*, 2006, 7(4):308-318.
Haagerup, A. et al. "Asthma and atopy—a total genome scan for susceptibility genes" *Allergy*, 2002, 57:680-686.
Hamad, A. et al. "Guanylyl cyclases, nitric oxide, antriuretic peptides, and airway smooth muscle function" *Am. J Physiol. Lung Cell. Mol. Physiol.*, 2003, 285:L973-L983.
Hulks, G. et al. "Influence of elevated plasma levels of atrial natriuretic factor on bronchial reactivity in asthma" *Am. Rev. Respir. Dis.*, 1991, 143:778-782, abstract.
Kato, N. et al. "Genetic analysis of the atrial natriuretic peptide gene in essential hypertension" *Clinical Science*, 2000, 98:251-258.
Mohapatra, S. et al. "Intranasal atrial natriuretic peptide (ANP) gene transfer attenuates airway reactivity in a mouse model of allergic asthma" *Journal of Clinical Immunology*, Feb. 1, 2003, 111(2):S309, abstract.
Nannipieri, M. et al. "Polymorphisms in the nANP (Human Atrial Natriuretic Peptide) Gene, Albuminuria, and Hyptertension" *Hypertension*, Jun. 2001, 37:1416-1422.
Nannipieri, M. et al. "Association between polymorphisms of the Atrial Natriuretic peptide gene and proteinuria: a population-based study" Diabetologia, 2003, 46:429-432.
Pandy, K.N. "Internalization and trafficking of guanylyl cyclase/natriuretic peptide receptor-A" *Peptides*, 2005, 26:985-1000.
Sakamoto, M. et al. "The Lung as a Possible Target Organ for Atrial Natriuretic Polypeptide Secreted from the Heart" Biochemical and Biophysical Research Communications, May 13, 1986, 135(2):515-520.
Schubert, S. et al. "Olignucleotide-Based Antiviral Strategies" *Handbook Exp Pharmacol*, 2006, 173:261-287.
Singam, R.V. et al. "Chitosan nanoparticle-mediated de novo synthesis of a novel natriuretic hormone peptide reverses established asthma in mice" *Journal of Allergy and Clinical Immunology*, Feb. 2004, 113(2):S325, abstract.
Xie, F.Y. et al. "Harnessing in vivo siRNA delivery for drug discovery and therapeutic development" *Drug Discovery Today*, Jan. 2006, 11(1/2):67-73.
Office Action dated Nov. 17, 2011 in U.S. Appl. No. 11/998,792, filed Nov. 30, 2007.
"Designing Custom Peptides" from Technical Bulletin of SIGMA Genosys, On World-wide Web.sigma-genosys.com/peptide_design.asp: accessed Dec. 16, 2004, 2 pages.
Benson, J.D. et al. "Validating cancer drug targets" *Nature*, May 2006, 441:451-456.
Berendsen, H.J.C. "A Glimpse of the Holy Grail?" *Science*, Oct. 23, 1998, 282(5389):642-643.
Bradley, C.M. et al. "Limits of Cooperativity in a Structurally Modular Protein: Response of the Notch Ankyrin Domain to Analogous Alanine Substitutions in Each Repeat" *J Mol Biol*, 2002, 324:373-386.
Brafford, P. et al. "Gene expression profiling of melanoma cells—searching the haystack" *Journal of Translational Medicine*, 2005, 3:2, pp. 1-2.
Carr, K.M. et al. "Gene-expression profiling in human cutaneous mellanoma" *Oncogene*, 2003, 22:3076-3080.
Chen, J.H. "Application of cationic polymer vector for gene delivery systems" *Yao Xue Xue Bao*, Apr. 2003, 38(4):316-20, abstract.
Chengalvala, M.V. et al. "Gene Expression Profiling and its Practice in Drug Development" *Current Genomics*, 2007, 8(4):262-270.
Chin, L. et al. "Malignant melanoma: genetics and therapeutics in the genomic era" *Genes & Development*, 2006, 20:2149-2182.

De Wit, N.J.W. et al. "Analysis of differential gene expression in human melanocytic tumour lesions by custom made oligoncucleotide arrays" *British Journal of Cancer*, 2005, 92:2249-2261.
Fluge, T. et al. "Bronochodilation using combined urodilatin-albuterol administration in asthma: a randomized, double-blind, placebo-controlled trial" *Eurpean Journal of Medical Research*, 1999, 4(10):411-415.
Gogas, H. et al. "Biomarkers in melanoma" *Annals of Oncology*, Aug. 2009, 20(Supplement 6):vi8-vi13.
Haberman, A.B. "Strategies to Move Beyond Target Validation" *Genetic Engineering News*, Dec. 2005, 25(21):36.
Ivanova, K. et al. "Differential Expression of Functional Guanylyl Cyclases in Melanocytes: Absence of Nitric-Oxide Isoform in Metastic Cells" *Journal of Investigative Dermatology*, Mar. 2001, 116(3):409-416.
Levy, J.A. et al. "Inactivation of Murine RNA Tumor Viruses by Isatin Beta-Thiosemicarbazone" *Virology*, Oct. 15, 1976, 74(2):426-431.
Lobbezoo, M.W. et al. "Signal Transduction Modulators for Cancer Therapy: From Promise to Practice?" *The Oncologist*, 2003, 8:210-213.
Martinez, S.R. et al. "Molecular Markers in Malignant Cutaneous Melanoma: Gift Horse or One-Trick Pony?" *Journal of Cellular Biochemistry*, 2005, 96:473-483.
Neidle, S. editor, "Failure Modes in the Discovery Process" *Cancer Drug Design and Discovery*, 2008, Elsevier/Academic Press, pp. 427-431.
Ngo, J.T. et al. "Computational Complexity, Protein Structure Prediction, and the Levinthal Paradox" *The Protein Folding Problem and Tertiary Structure Prediction*, 1994, Birkhäuser Boston, Le Grand Edition, pp. 491-495.
Pandey, K.N. et al. "Molecular Cloning and Expression of Murine Guanylate Cyclase/Atrial Natriuretic Factor Receptor cDNA" *The Journal of Biological Chemistry*, Jul. 25, 1990, 265(21):12342-12348.
Rahmanto, Y.S. et al. "Identification of distinct changes in gene expression after modulation of melanoma tumor antigen p97 (melanotransferrin) in mulitple models in vitro and in vivo" *Carcinogenesis*, 2007, 28(10):2172-2183.
Rudinger, J. "Charactieristics of the amino acids as components of a peptide hormone sequence" *Peptide Hormones*, Biological Council: The Co-ordinating Committee for Symposia on Drug Action; J.A. Parsons, editor; Baltimore: University Park Press, Jun. 1976, pp. 1-7.
Schinzel, R. et al. "The phosphate recognition site of *Escherichia coli* maltodextrin phosphorylase" *FEBS Letters*, Jul. 1991, 286(1 and 2):125-128.
Schwab, G. et al. "An approach for new anticancer drugs: Oncogene-targeted antisense DNA" *Ann Oncol*, 1994, 5(Supplement 4):S55-S58.
Seftor, E.A. et al. "Expression fo multiple molecular phenotypes by aggressive melanoma tumor cells: role in vasculogenic mimicry" *Critical Reviews in Oncology/Hemtology*, 2002, 44:17-27.
Skubitz, A.P.N. et al. "Differential gene expression identifies subgroups of ovarian carcinoma" *Translational Research*, Nov. 2006, 148(5):223-248.
Sporn, M.B. et al. "Chemoprevention of cancer" *Carcinogenesis*, 2000, 21(3):525-530.
Sprenger, H. et al. "The lack of receptors for atrial natriuretic peptides on human moncytes prevents a rise of cGMP and induction of tumor necrosis factor-alpha synthesis" *Immunobiology*, Sep. 1991, 183(1-2):94-101.
Sun, Y. et al. "Atrial Natriuretic Peptide and Long Acting Natriuretic Peptide Inhibit ERK 1/2 in Prostate Cancer Cells" *Anticancer Research*, 2006, 26:4143-4148.
Sun, Y. et al. "Vessel Dilator and Kaliuretic Peptide Inhibit ERK 1/2 Activation in Human Prostate Cancer Cells" *Anticancer Research*, 2006, 26:3217-3222.
Vesely, D.L. et al. "The N-Terminus of the Atrial Natriuretic Factor Prohormone in the Pleural Fluid of Congestive Heart Failure Patients" *Chest*, 1990, 97(6):1295-1298.

(56) References Cited

OTHER PUBLICATIONS

Vesely, D.L. "Aprotinin blocks the binding of pro atrial natriuretic peptides 1 to 30, 31 to 67, and 99-126 to human placental membranes" *Am J Obstet Gynecol*, 1991, 165(3)567-573.

Vesely, D.L. "Atrial Natriuretic Hormones Originating from the N-Terminus of the Atrial Natriuretic Factor Prohormone" *Clin Exp Pharmacol Physiol*, 1995, 22(2):108-114.

Vesely, D.L. et al. "Long-Acting Natriuretic Peptide, Vessel Dilator, and Kaliuretic Peptide Enhance the Urinary Excretion Rate of $\beta_2$-Microglobulin" *Metabolism*, Dec. 2000, 49(12):1592-1597.

Vesely, D.L. "Atrial natriuretic peptides: anticancer agents" *J Investig Med.*, 2005, 53(7):360-365.

Vita, M. et al. "The Myc oncoprotein as a therapeutic target for human cancer" *Seminars in Cancer Biology*, 2006, 16:318-330.

Voet, D. et al. editors, "Section 9-3: Abnormal Hemoglobins" *Biochemistry*, 2nd Edition; New York: John Wiley & Sons, 1995, pp. 235-241.

Winnepennickx, V. et al. "Gene Expression Profiling of Primary Cutaneous Melanoma and Clinical Outcome" *Journal of the National Cancer Institute*, Apr. 5, 2006, 98(7):472-482.

Wong, H.H. et al. "Pancreatic cancer: molecular pathogenesis and new therapeutic targets" *Nat Rev Gastroenterol Hepatol*, 2009, 6:412-422.

Yang, J. et al. "Conditional ablation of *Ikkb* inhibits melanoma tumor development in mice" *The Journal of Clinical Investigation*, Jul. 2010, 120(7):2563-2574.

U.S. Appl. No. 13/604,467, filed Sep. 5, 2012, Mohapatra et al.

* cited by examiner

FIG. 2A
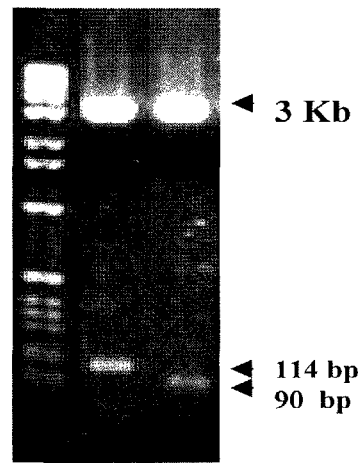
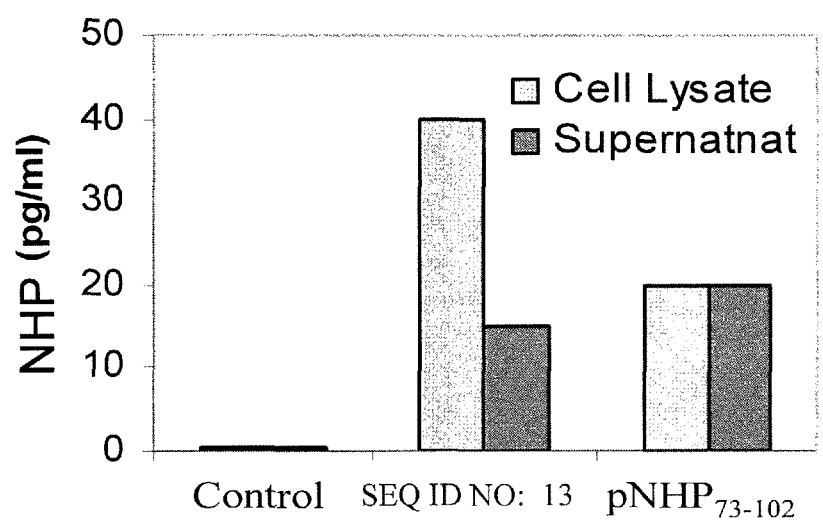
FIG. 2B

FIG. 3A
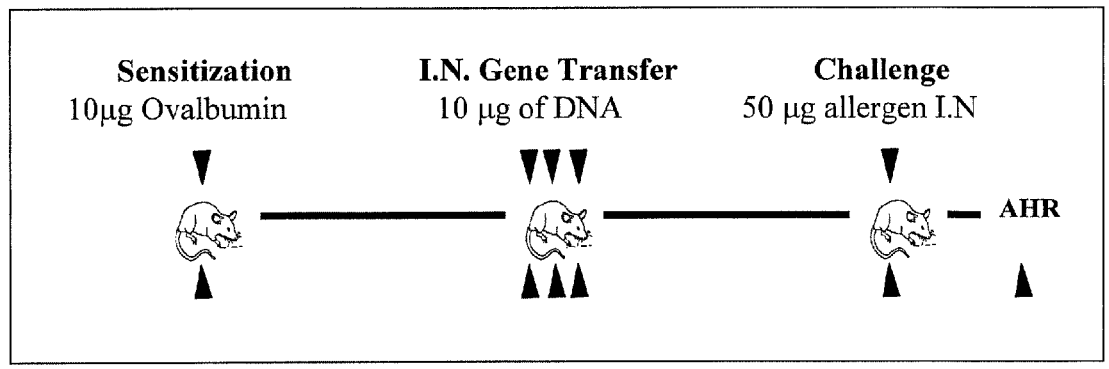
FIG. 3B
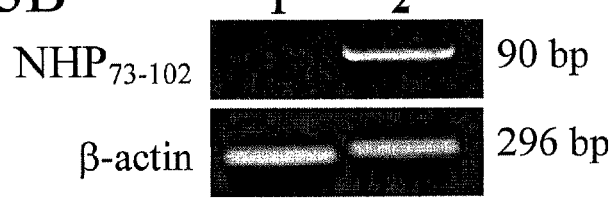
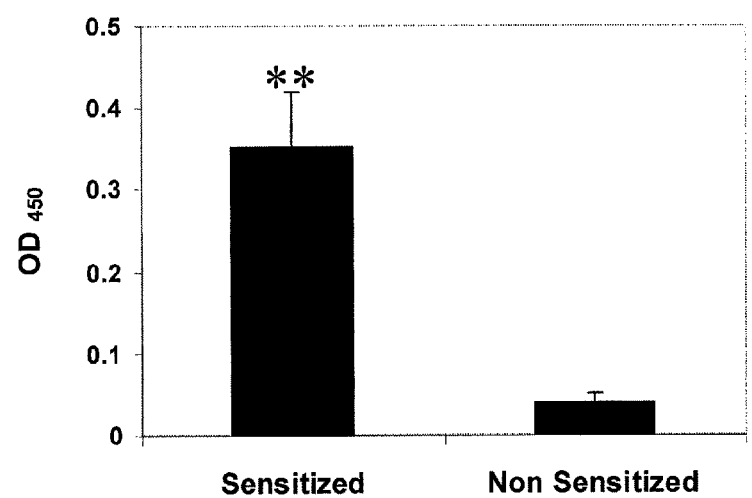
FIG. 3C

FIG. 6A
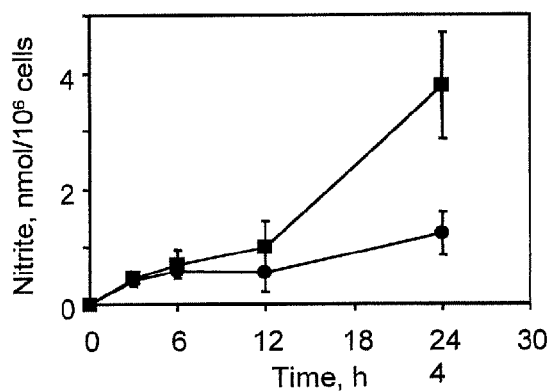
FIG. 6B
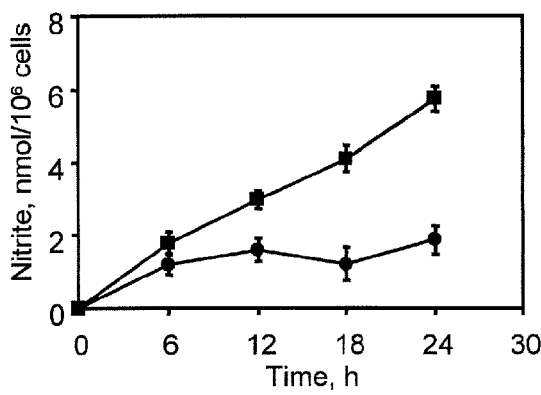
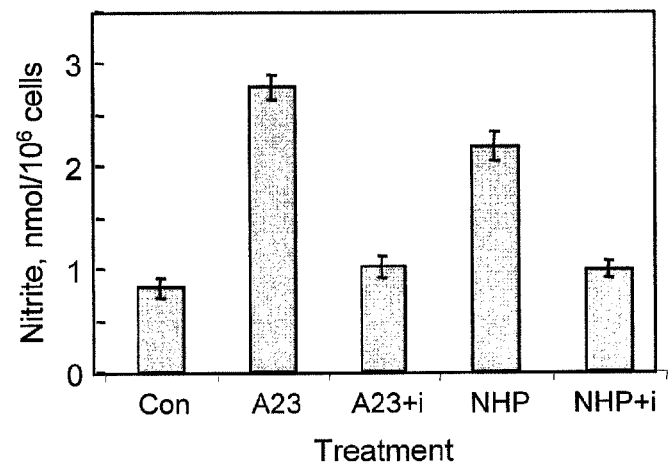
FIG. 6C

MATERIALS AND METHODS FOR TREATMENT OF RESPIRATORY ALLERGIC DISEASES

CROSS-REFERENCE TO RELATED APPLICATIONS

The present application is a divisional of U.S. application Ser. No. 10/526,584, filed Mar. 3, 2005, now U.S. Pat. No. 7,655,772, which is a National Stage filing of International Application Number PCT/US2003/028056, filed Sep. 8, 2003, which claims the benefit of U.S. Provisional Application No. 60/319,529, filed Sep. 6, 2002, each of which is hereby incorporated by reference herein in its entirety, including any figures, tables, nucleic acid sequences, amino acid sequences, or drawings.

BACKGROUND OF THE INVENTION

Respiratory diseases, such as allergic rhinitis, asthma, and chronic obstructive pulmonary disorders (COPD) are often debilitating conditions with high prevalence, affecting more than 155 million people in the developed world. Asthma is one of the common chronic diseases and is rapidly increasing by 20% to 50% per decade, particularly in children. Currently, there are 53 million patients in the major pharmaceutical markets. Constriction of the airways is the hallmark of chronic conditions such as asthma and COPD, and inflammation is common to all respiratory diseases affecting either the upper or lower airways. Bronchodilators, which may possess limited anti-inflammatory activity, are considered the first line of therapy for asthma. Steroids are considered the gold standard as anti-inflammatory therapy, but they possess other significant adverse effects. Effective therapeutics other than steroids are under intense investigation.

A group of four peptide hormones, originating from the 126-amino acid atrial natriuretic factor (ANF) prohormone, have been known for their vasodilator activity. These four peptide hormones, consisting of amino acids 1-30, 31-67, 79-98, and 99-126 of this prehormone, have been named long acting natriuretic peptide, vessel dilator, kaliuretic peptide, and atrial natriuretic peptide (ANP), respectively for their most prominent effects (Angus R. M. et al., *Clin Exp Allergy* 1994, 24:784-788). The ANP sequence, particularly the C-terminal portion, is highly conserved among species (Seidman et al., *Science*, 1984, 226:1206-1209). It has been proposed to be useful for treatment of various cardiovascular, respiratory, cancerous and renal diseases (Vesely, D. L. *Cardiovascular*, 2001, 51:647-658).

The C-terminal peptide of proANF (also known by the synonym proANP), ANP is a 28-amino acid hormone secreted by the cardiac atria and lung tissue (Needleham, P. et al., *N Engl J Med*, 1986, 314:828-834). ANP has vasodilator, natriuretic and diuretic properties (Needleham, P. et al., *N Engl J Med*, 1986, 314:828-834). ANP infused at high concentrations reduces airway resistance in normal subjects (Hulks G. et al., *Clin Sci* 1990; 79:51-55) and produces a significant bronchodilator response in patients with asthma. Inhaled ANP attenuates histamine- and methacholine (MCh)-induced bronchoconstriction (Hulks, G. et al., *Br. Med. J*, 1992, 304:1156; Angus, R. M. et al., *Clin Exp Allergy*, 1994, 24:784-788); however, the amount of ANP required for efficacy and their short half-life limits their use for long-term modulation of airway hyper-responsiveness (Harnet, P. et al., *Nephrologie*, 1987, 8:7-12; Matsuse, H., et al., *J Immunol*, 2000, 164:6583-6582).

The present inventor has demonstrated prolonged amelioration of symptoms associated with respiratory allergy and asthma by delivery of pDNA-encoding various natriuretic hormone peptides (NHPs), or by delivery of the peptides themselves, which exhibit bronchodilatory and/or anti-inflammatory activity.

BRIEF SUMMARY OF THE INVENTION

The present invention pertains to a method for treating respiratory allergies, such as allergic rhinitis and asthma, which may be caused by allergens and exacerbated by respiratory viral infections, pollutants, and smoke.

In one embodiment, the method of the present invention comprises administering a therapeutically effective amount of a natriuretic hormone peptide (referred to herein as NHP or NHP peptide) to a patient in need of such treatment. As used herein, NHP refers to atrial natriuretic factor (ANF) hormone, or a biologically active fragment or homolog thereof.

Specifically exemplified NHPs comprise an amino acid sequence selected from the group consisting of amino acids 1-30 of ANF (also known as "long acting natriuretic peptide" and referred to herein as $NHP_{1-30}$ or SEQ ID NO:1), amino acids 31-67 of ANF (also known as "vessel dilator" and referred to herein as $NHP_{31-67}$ or SEQ ID NO:2), amino acids 79-98 of ANF (also known as "kaliuretic peptide" and referred to herein as $NHP_{79-98}$ or SEQ ID NO:3), and amino acids 99-126 of ANF (also known as "atrial natriuretic peptide" or "ANP", and referred to herein as $NHP_{99-126}$ or SEQ ID NO:4), or biologically active fragments or homologs of any of the foregoing. Other exemplified NHPs comprise amino acids 73-102 of proANF (referred to herein as $NHP_{73-102}$ or SEQ ID NO:5), or SEQ ID NO:6, or biologically active fragment(s) or homolog(s) of the foregoing. In one embodiment, the NHP administered to the patient does not consist of $NHP_{99-126}$ (SEQ ID NO:4).

In another embodiment, the method of the present invention comprises administering an effective amount of at least one nucleic acid molecule encoding an NHP to a patient in need of such treatment. The present inventor has determined that introduction of a nucleic acid molecule encoding NHP is capable of inhibiting allergen-specific IgE synthesis for the treatment of allergic disease. The gene delivery method of the present invention permits long-term expression of NHP-encoding nucleic acid sequences in vivo, thereby conferring bronchoprotective effect and/or anti-inflammatory effect against respiratory allergies, such as asthma. In one embodiment, a therapeutically effective amount of at least one nucleic acid molecule encoding a peptide comprising an amino acid sequence selected from the group consisting of SEQ ID NO:1, SEQ ID NO:2, SEQ ID NO:3, SEQ ID NO:4, SEQ ID NO:5, and SEQ ID NO:6 or biologically active fragments or homologs of any of the foregoing, are administered to the patient.

In another aspect, the present invention concerns an isolated peptide comprising the amino acid sequence $NHP_{73-102}$ (SEQ ID NO:5) or SEQ ID NO:6, or a biologically active fragment or homolog of the foregoing. In another aspect, the present invention concerns an isolated nucleic acid molecule encoding the amino acid sequence of $NHP_{73-102}$ (SEQ ID NO:5) or encoding the amino acid sequence of SEQ ID NO:6, or a biologically active fragment or homolog thereof.

In another aspect, the present invention concerns an expression vector comprising a nucleic acid sequence encoding an NHP, and a promoter sequence that is operably linked to the NHP-encoding nucleic acid sequence. In one embodiment, the expression vector is a DNA plasmid or virus. In another aspect, the present invention concerns a pharmaceutical composition comprising a nucleic acid sequence encoding an NHP, and a pharmaceutically acceptable carrier.

BRIEF DESCRIPTION OF THE DRAWINGS

For a fuller understanding of the nature and objects of the invention, reference should be made to the following detailed description, taken in connection with the accompanying drawings, in which:

FIGS. 2A and 2B show cloning and expression of NHP in human alveolar cells and effect on AHR of murine lung. FIG. 2A shows the successful cloning of the peptides of ANF in the pVAX expression vector. The gel electrophoresis of excised inserts corresponding to SEQ ID NO:13 (approximately 114 bp band) and to $NHP_{73-102}$ (approximately 90 bp band) are shown. FIG. 2B shows expression of $NHP_{73-102}$ in human Type II alveolar epithelial cells, A549. A549 cells were either transfected with $pNHP_{73-102}$, SEQ ID NO:13 or pVAX vector control. Expression of ANP-like peptide was detected in cell supernatant and lysate from transfected cells alone but not pVAX control. *$p<0.05$; compared to pVAX control.

FIGS. 3A-3E show therapeutic effect of $NHP_{73-102}$ on asthma in mice. FIG. 3A shows an experimental outline of immunization protocol using $NHP_{73-102}$. FIG. 3B shows expression of $NHP_{73-102}$ in murine lung. Mice were administered intranasally (i.n.) either with $pNHP_{73-102}$ or pVAX as described. Three days following the last DNA administration, NHP expression was checked from lung tissue by RT-PCR. Mice receiving $NHP_{73-102}$ (lane 2) exhibited NHP expression, which was not present in control mice receiving empty pVAX plasmid (lane 1). FIG. 3C shows an estimation of the degree of sensitization following ova injection (FIG. 3A). Mice (n=4) were injected intraperitonealy (i.p.) either with ova and alum or phosphate buffered saline (PB), and on day 21 their serum was analyzed for ova specific IgE. Mice receiving ova and alum exhibited higher titers ($p<0.01$) of ova specific IgE than the PBS control. The experiments were repeated twice and data from a representative experiment are shown. FIG. 3D-E show the measurement of AHR to increasing concentrations of methacholine following NHP gene transfer on day 26. BALB/c mice (n=4) were sensitized with ovalbumin by i.p. immunization (10 μg/mouse) and 14 days later were treated with 10 μg/mouse of SEQ ID NO:13 or $pNHP_{73-102}$ intranasally. The control group received the empty vector alone. Each mouse was intranasaly administered three times on two days interval with 10 μg of plasmid DNA complexed with 50 μg of transfection reagent Lipofectamine (Life Technologies, Rockville, Md.). Animals were challenged with the same allergen (50 μg in PBS) three days after the last intransal DNA delivery and 24 hours later their AHR was measured using the whole body plethysmograph (Buxco, Troy, N.Y.). A dose-dependent decrease of methacholine response is shown in FIG. 3D. FIG. 3E shows the effect of treatment with SEQ ID NO:13 and $pNHP_{73-102}$ on allergen-induced airway hyper-responsiveness (AHR). The effect of treatment at the highest concentration (50 mg/ml) of methacholine challenge is shown ($p<0.05$).

FIG. 4A shows schematically the protocol of sensitization, treatment and antigen challenges and measurement of AHR. FIG. 4B shows measurement of Penh (%) at 50 mg/ml of methacholine. *$p<0.05$; compared to pVAX control. The experiment was repeated twice and data from a representative experiment are shown.

FIG. 5A shows an experimental outline of immunization protocol with allergen and RSV, treatment schedules, challenges and AHR measurements. FIG. 5B shows reversal of airway hyper-reactivity as evident from % Penh measurement following treatment with chitosan+$pNHP_{73-102}$. The other treatments include chitosan+pVAX (control), chitosan+$NHP_{73-102}$, fluticasone, and fluticasone and salmeterol alone. FIG. 5C shows the reduction in inflammatory cells in the lung by treatment with $pNHP_{73-102}$. Mice treated as shown in FIG. 5B were subjected to bronchioalveolar lavage (BAL) following AHR. A BAL cell differential was performed and cytospun BAL cells were stained and different cell types were quantified by three blinded investigators. The percentage of cells of macrophages, eosinophils, neutrophils and lymphocytes were determined.

FIGS. 6A-6C show that overexpression of $NHP_{73-102}$ leads to increased production of nitric oxide in human epithelial cells. A549 (FIG. 6A) and NHBE (FIG. 6B) cells were transfected with control vector or $NHP_{73-102}$. At the indicated times after transfection, aliquots of the culture medium were assayed for nitrite (the NO reaction product). Fluorescence was read at 409 nm with excitation at 365 nm using a JASCO spectrofluorometer. Data are means±SEM (n=3). FIG. 6C shows that NO production is due to the constitutive NOS. One aliquot of cells was incubated during the expression phase with 1 mM $N_\omega$-nitro-L-arginine methyl ester, an arginine analog that blocks cNOS production of NO(NHP+i). The enhanced NO generation was inhibited by pretreatment of the cells with N-nitro-L-arginine methyl ester, which blocks cNOS activity.

BRIEF DESCRIPTION OF THE SEQUENCES

Figure 1:
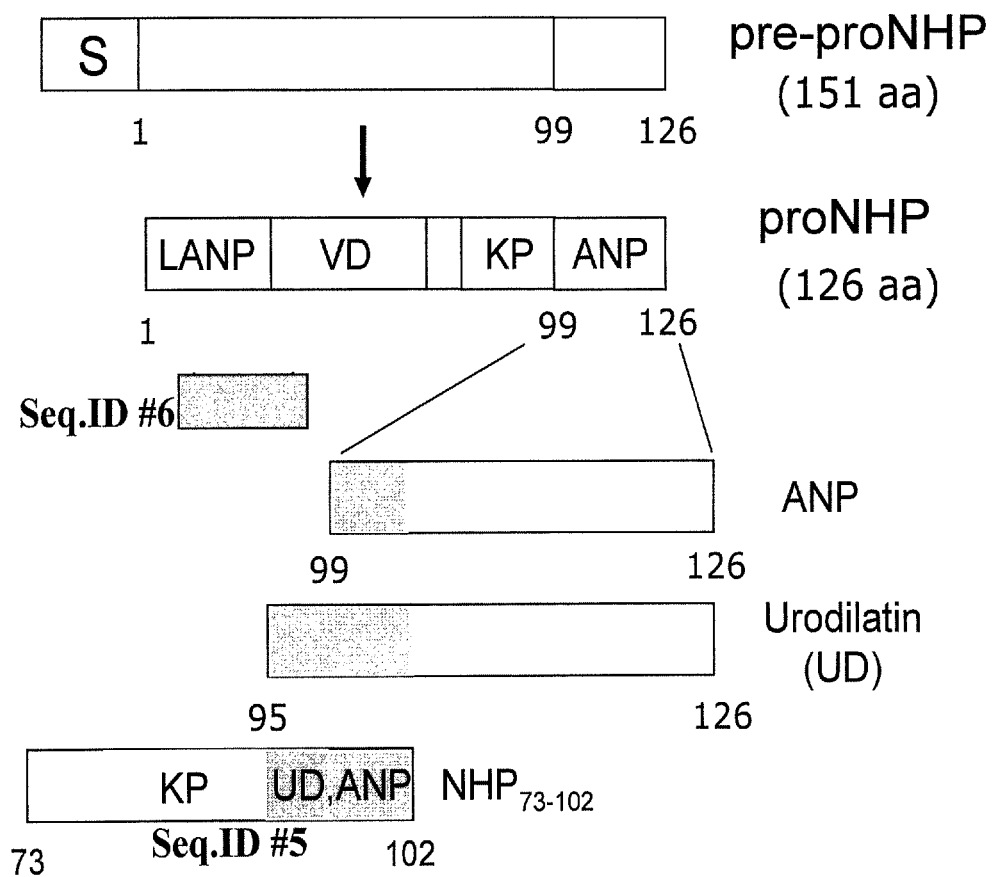
FIG. 1 shows a diagram depicting the family of natriuretic hormone peptides (NHP). Translation of the atrial natriuretic factor gene results in a pre-prohormone from which the 5' signal sequence is cleaved to yield the 126 amino acid prohormone (ANF). The prohormone is further cleaved by endopeptidases into several bioactive peptides, long-acting natriuretic peptide (LANP) ($NHP_{1-30}$; SEQ ID NO:1), vessel dialator (VD) ($NHP_{31-67}$; SEQ ID NO:2), kaliuretic peptide (KP) ($NHP_{79-98}$; SEQ ID NO:3), and atrial natriuretic peptide (ANP) ($NHP_{99-126}$; SEQ ID NO:4). Urodialatin (UD), a variant of ANP is also in circulation and has been implicated in asthma. The NHP construct used in these studies encodes $NHP_{73-102}$ (SEQ ID NO:5) and SEQ ID NO:6, which are distinct from the above peptides but include a critical overlap region shared with UD and ANP.

SEQ ID NO:1 is the amino acid sequence of human "long acting natriuretic peptide" or $NHP_{1-30}$:

$^{1}$NPMYN AVSNADLMDF KNLLDHLEEK MPLED$^{30}$.

SEQ ID NO:2 is the amino acid sequence of human "vessel dilator" or $NHP_{31-67}$:

$^{31}$EVVPP QVLSEPNEEA GAALSPLPEV PPWTGEVSPA QR$^{67}$.

SEQ ID NO:3 is the amino acid sequence of human "kaliuretic peptide" or $NHP_{79-98}$:

$^{79}$SSDRSAL LKSKLRALLT APR$^{98}$.

SEQ ID NO:4 is the amino acid sequence of human "atrial natriuretic peptide" (ANP) or $^{99}$SLRRSSC FGGRMDRIGA QSGLGCNSFR Y$^{126}$.

SEQ ID NO:5 is the amino acid sequence of cloned mouse $pNHP_{73-102}$:

$^{73}$GSPWDPSDRSALLKSKLRALLAGPRSLRRS$^{102}$.

SEQ ID NO:6 is the amino acid sequence of cloned mouse NHP fragment:

VSNTDLMDFKNLLDHLEEKMPVEDEVMPPQALSEQTE.

SEQ ID NO:7 is the amino acid sequence for the human preproANP (NCBI ACCESSION # NM_006172) wherein the underlined amino acids represent the signal sequence which is cleaved off to form the mature peptide:

$^{1}$<u>MSSFSTTTVS FLLLLAFQLL GQTRAN</u>PMYN AVSNADLMDF

KNLLDHLEEK MPLEDEVVPP QVLSEPNEEA GAALSPLPEV

PPWTGEVSPA QRDGGALGRG PWDSSDRSAL LKSKLRALLT

APRSLRRSSC FGGRMDRIGA QSGLGCNSFR Y$^{151}$.

SEQ ID NO:8 is a forward primer for the cDNA sequence encoding mouse prepro ANF protein:

5'-gac ggc <u>aag ctt</u> act atg ggc agc ccc tgg gac cc-3'.

SEQ ID NO:9 is a reverse primer for the cDNA sequence encoding mouse pre-proANF protein:

5'-acc ccc <u>ctc gag</u> tta tta tct tcg tag gct ccg-3'.

SEQ ID NO:10 is a forward primer for the cDNA sequence encoding mouse NHP fragment:

5'-aat cct aag ctt agt atg gtg tcc aac aca gat-3'

SEQ ID NO:11 is a reverse primer for the cDNA sequence encoding mouse NHP fragment:

5'- tgc gaa ctc gag tta ctc agt ctg ctc act cag ggc ctg cg-3'

SEQ ID NO:12 is the nucleotide sequence encoding cloned mouse $pNHP_{73-102}$:

atg ggc agc ccc tgg gac ccc tcc gat aga tct gcc ctc ttg aaa agc aaa ctg agg gct ctg ctc gct ggc cct cgg agc cta cga aga taa SEQ ID NO:13 is the nucleotide sequence encoding cloned mouse pNHP fragment:

atg gtg tcc aac aca gat ctg atg gat ttc aag aac ctg cta gac cac ctg gag gag aag atg ccg gta gaa gat gag gtc atg ccc ccg cag gcc ctg agt gag cag act gag taa SEQ ID NO:14 is the mRNA nucleotide sequence encoding human ANP (NCBI Accession # NM_006172:

```
  1 tggcgaggga cagacgtagg ccaagagagg ggaaccagag aggaaccaga ggggagagac
 61 agagcagcaa gcagtggatt gctccttgac gacgccagca tgagctcctt ctccaccacc
121 accgtgagct tcctcctttt actggcattc cagctcctag gtcagaccag agctaatccc
181 atgtacaatg ccgtgtccaa cgcagacctg atggatttca agaatttgct ggaccatttg
241 gaagaaaaga tgccttttaga agatgaggtc gtgcccccac aagtgctcag tgagccgaat
301 gaagaagcgg gggctgctct cagccccctc cctgaggtgc ctccctggac cggggaagtc
361 agcccagccc agagagatgg aggtgccctc gggcggggcc cctgggactc ctctgatcga
421 tctgccctcc taaaaagcaa gctgagggcg ctgctcactg cccctcggag cctgcggaga
481 tccagctgct cggggggcag gatggacagg attggagccc agagcggact gggctgtaac
541 agcttccggt actgaagata acagccaggg aggacaagca gggctgggcc tagggacaga
601 ctgcaagagg ctcctgtccc ctgggtctc tgctgcattt gtgtcatctt gttgccatgg
```

-continued

```
661 agttgtgatc atcccatcta agctgcagct tcctgtcaac acttctcaca tcttatgcta 721 actgtagata aagtggtttg atggtgactt cctcgcctct cccaccccat gcattaaatt 781 ttaaggtaga acctcacctg ttactgaaag tggtttgaaa gtgaataaac ttcagcacca 841 tggac
```

SEQ ID NO:15 is the human gene for atrial natriuretic factor propeptide (coding sequence includes—join (570 . . . 692, 815 . . . 1141, 2235 . . . 2240); sig. peptide=570 . . . 644; mat. peptide=join (645 . . . 692, 815 . . . 1141, 2235 . . . 2237), (NCBI ACCESSION NO: X01471; Greenberg, B. D. et al., *Nature*, 1984, 312(5995):656-658):

```
   1 ggatccattt gtctcgggct gctggctgcc tgccatttcc tcctctccac ccttatttgg 61 aggccctgac agctgagcca caaacaaacc aggggagctg ggcaccagca agcgtcaccc 121 tctgtttccc cgcacggtac cagcgtcgag gagaaagaat cctgaggcac ggcggtgaga 181 taaccaagga ctcttttta ctcttctcac acctttgaag tgggagcctc ttgagtcaaa 241 tcagtaagaa tgcggctctt gcagctgagg gtctgggggg ctgttgggc tgcccaaggc 301 agagaggggc tgtgacaagc cctgcggatg taaactttaa aagggcatct cctgctggct 361 tctcacttgg cagctttatc actgcaagtg acagaatggg gagggttctg tctctcctgc 421 gtgcttggag agctgggggg ctataaaaag aggcggcact gggcagctgg agacaggga 481 cagacgtagg ccaagagagg ggaaccagag aggaaccaga ggggagagac agagcagcaa 541 gcagtggatt gctccttgac gacgccagca tgagctcctt ctccaccacc accgtgagct 601 tcctcctttt actggcattc cagctcctag gtcagaccag agctaatccc atgtacaatg 661 ccgtgtccaa cgcagacctg atggatttca aggtagggcc aggaaagcgg gtgcagtctg 721 gggccagggg gctttctgat gctgtgctca ctcctcttga tttcctccaa gtcagtgagg 781 tttatccctt tccctgtatt ttccttttct aaagaatttg ctggaccatt tggaagaaaa 841 gatgccttta aagatgaggg tcgtgccccc acaagtgctc agtgagccga atgaagaagc 901 gggggctgct ctcagccccc tccctgaggt gcctccctgg accggggaag tcagcccagc 961 ccagagagat ggaggtgccc tcgggcgggg cccctgggac tcctctgatc gatctgccct 1021 cctaaaaagc aagctgaggg cgctgctcac tgcccctcgg agcctgcgga gatccagctg 1081 cttcggggc aggatggaca ggattggagc ccagagcgga ctgggctgta acagcttccg 1141 ggtaagagga actggggatg gaaatgggat gggatggaca ctactgggag acaccttcag 1201 caggaaaggg accaatgcag aagctcattc cctctcaagt ttctgcccca acacccagag 1261 tgccccatgg gtgtcaggac atgccatcta ttgtccttag ctagtctgct gagaaaatgc 1321 ttaaaaaaaa aagggggggg gctgggcacg gtcgtcacgc ctgtaatccc agcactttgg 1381 gaggccaggc agcggatcat gaggtcaaga gatcaagact atcctggcca acatggtgaa 1441 accccagctc tactaaaaat acaaaaatta gctgggtgtg tggcgggcac ctgtactctc 1501 agctacttgg gaggctgagg caggagaatc acttgaaccc aggaggcaga ggttgcagtg 1561 agcagagatc acgccactgc agtccagcct aggtgataga gcgagactgt ctcaaaaaaa 1621 aaaaaaaaag gccaggcgcg gtggctcacg cctgtaatcc cagcgctttg ggaggccaag 1681 gcgggtggat cacgaggtca ggagatggag accatcctgg ctaacacggt gaaaccccgt 1741 ctctactaaa aatacaaaaa attagccagg cgtggtggca ggcgcctgta agtcctagct 1801 actccggagg ctgaggcagg agaatggcgt gaacccggga ggcggagctt gcagtgagca 1861 gagatgcac cactgcactc cagcctgggc gacagagcaa gactccgtct caaaaaaaa 1921 aaaaaaaaa gcaactgcca ctagcactgg gaaattaaaa tattcataga gccaagttat
```

```
1981 ctttgcatgg ctgattagca gttcatattc ctccccagaa ttgcaagatc ctgaagggct 2041 taagtgaaat ttactctgat gagtaacttg cttatcaatt catgaagctc agagggtcat 2101 caggctgggg tgggggccgg tgggaagcag gtggtcagta atcaagttca gaggatgggc 2161 acactcatac atgaagctga cttttccagg acagccaggt caccaagcca gatatgtctg 2221 tgttctcttt gcagtactga agataacagc cagggaggac aagcagggct gggcctaggg 2281 acagactgca agaggctcct gtcccctggg gtctctgctg catttgtgtc atcttgttgc 2341 catggagttg tgatcatccc atctaagctg cagcttcctg tcaacacttc tcacatctta 2401 tgctaactgt agataaagtg gtttgatggt gacttcctcg cctctcccac cccatgcatt 2461 aaattttaag gtagaacctc acctgttact gaaagtggtt tgaaagtgaa taaacttcag 2521 caccatggac agaagacaaa tgcctgcgtt ggtgtgcttt ctttcttctt gggaagagaa 2581 ttc
```

SEQ ID NO:16 is the amino acid sequence for the mouse preproANP peptide

```
  1 mgsfsitlgf flvlafwlpg higanpvysa vsntdlmdfk nlldhleekm pvedevmppq
 61 alseqteeag aalsslpevp pwtgevnppl rdgsalgrsp wdpsdrsall ksklrallag
121 prslrrsscf ggridrigaq sglgcnsfry rr
```

SEQ ID NO:17 is the genetic sequence for the mouse preproANP peptide wherein the coding sequence starts at nucleic acid molecule position 81 and ends at nucleic acid molecule position 539.

```
  1 caaaagctga gagagagaga gaaagaaacc agagtgggca gagacagcaa acatcagatc
 61 gtgccccgac ccacgccagc atgggctcct tctccatcac cctgggcttc ttcctcgtct
121 tggccttttg gcttccaggc catattggag caaatcctgt gtacagtgcg gtgtccaaca
181 cagatctgat ggatttcaag aacctgctag accacctgga ggagaagatg ccggtagaag
241 atgaggtcat gccccgcag gccctgagtg agcagactga ggaagcaggg gccgcactta
301 gctccctccc cgaggtgcct ccctggactg gggaggtcaa cccacctctg agagacggca
361 gtgctctagg gcgcagcccc tgggacccct ccgatagatc tgccctcttg aaaagcaaac
421 tgagggctct gctcgctggc cctcggagcc tacgaagatc cagctgcttc gggggtagga
481 ttgacaggat tggagcccag agtggactag gctgcaacag cttccggtac cgaagataac
541 agccaaggag gaaaaggcag tcgattctgc ttgagcagat cgcaaaagat cctaagccct
601 tgtggtgtgt cacgcagctt ggtcacattg ccactgtggc gtggtgaaca ccctcctgga
661 gctgcggctt cctgccttca tctatcacga tcgatgttaa atgtagatga gtggtctagt
721 ggggtcttgc ctctcccact ctgcatatta aggtagatcc tcacccttt cagaaagcag
781 ttggaaaaaa aaaaaagaa taaacttcag caccaaggac agacgccgag gccctgatgt
841 gcttctttgg cttctgccct cagttctttg ctctcccc
```

SEQ ID NO:18 is the nucleotide sequence encoding the amino acid sequence of SEQ ID NO: 5:

ggc agc cce tgg gac ccc tcc gat aga tct gcc ctc ttg aaa agc aaa ctg agg gct ctg ctc gct ggc cct cgg agc eta cga aga tcc SEQ ID NO:19 is the nucleotide sequence encoding the amino acid sequence of SEQ ID NO: 6:

gtg tcc aac aca gat ctg atg gat ttc aag aac ctg cta gac cac ctg gag gag aag atg ccg gta gaa gat gag gtc atg ccc cgc cag gcc ctg agt gag cag act gag

DETAILED DISCLOSURE

The present invention pertains to a method for treating allergen-induced airway reactivity by administering a natriuretic hormone peptide (NHP), or a nucleic acid sequence encoding an NHP, to a patient in need thereof, thereby ameliorating airway hyper-reactivity and/or airway inflammation, which are characteristic of respiratory allergic disease, such as allergic rhinitis and asthma.

In specific embodiments, the peptides used in the subject invention comprise at least one amino acid sequence selected from the group consisting of $NHP_{1-30}$, $NHP_{31-67}$, $NHP_{79-98}$, and $NHP_{73-102}$, (SEQ ID NO:1, SEQ ID NO:2, SEQ ID NO:3, and SEQ ID NO:5, respectively), SEQ ID NO:6, or a biologically active fragment or homolog thereof. In some embodiments, a combination of NHP or NHP-encoding nucleic acid sequences is utilized. In one embodiment, the peptide utilized does not consist of the amino acid sequence of $NHP_{99-126}$ (SEQ ID NO:4). In other embodiments, the peptides used in the subject invention comprise at least one amino acid sequence selected from the group consisting of SEQ ID NO:7, and SEQ ID NO:16, or biologically active fragments or homologs of any of the foregoing.

According to the gene therapy method of the present invention, the NHP-encoding nucleic acid sequence is preferably administered to the airways of the patient, e.g., nose, sinus, throat and lung, for example, as nose drops, by nebulization, vaporization, or other methods known in the art. More preferably, the nucleic acid sequence encoding NHP is administered to the patient orally or intranasally, or otherwise intratracheally. For example, the nucleic acid sequence can be inhaled by the patient through the oral or intranasal routes, or injected directly into tracheal or bronchial tissue.

In specific embodiments, the nucleic acid sequences used in the subject invention encode at least one amino acid sequence selected from the group consisting of $NHP_{1-30}$, $NHP_{31-67}$, $NHP_{79-98}$, $NHP_{99-126}$, and $NHP_{73-102}$, (SEQ ID NO:1, SEQ ID NO:2, SEQ ID NO:3, SEQ ID NO:4, and SEQ ID NO:5, respectively), SEQ ID NO:6, or a biologically active fragment or homolog of any of the foregoing. In other embodiments, the nucleic acid sequences used in the subject invention comprise at least one nucleotide sequence selected from the group consisting of SEQ ID NO:12, SEQ ID NO:13, SEQ ID NO:14, SEQ ID NO:15, and SEQ ID NO:17, or a biologically active fragment or homolog of any of the foregoing.

Preferably, the nucleic acid sequence encoding the NHP is administered with a nucleic acid sequence that is operatively linked with the NHP-encoding nucleic acid sequence and operates as a regulatory sequence. For example, the regulatory sequence can be a promoter sequence that controls transcription and drives expression of the NHP-encoding nucleic acid sequence at the desired site, such as at, or adjacent to, the patient's respiratory epithelial cells. The promoter can be a constitutive or inducible promoter to allow selective transcription. The promoter can be a vertebrate or viral promoter. Optionally, enhancers may be used to obtain desired transcription levels. An enhancer is generally any non-translated nucleic acid sequence that works contiguously with the coding sequence (in cis) to change the basal transcription level dictated by the promoter.

The NHP-encoding nucleic acid sequences used in the methods, expression vectors, and pharmaceutical compositions of the present invention are preferably isolated. According to the present invention, an isolated nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule or sequence useful in the present composition can include DNA, RNA, or any derivatives of either DNA or RNA. An isolated nucleic acid molecule or sequence can be double stranded (i.e., containing both a coding strand and a complementary strand) or single stranded.

A nucleic acid molecule can be isolated from a natural source, or it can be produced using recombinant DNA technology (e.g., polymerase chain reaction (PCR) amplification, cloning) or chemical synthesis. Nucleic acid molecules can be generated or modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules, and combinations thereof.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. As used herein, a "coding" nucleic acid sequence refers to a nucleic acid sequence that encodes at least a portion of a peptide or protein (e.g., a portion of an open reading frame), and can more particularly refer to a nucleic acid sequence encoding a peptide or protein which, when operatively linked to a transcription control sequence (e.g., a promoter sequence), can express the peptide or protein.

The term "operably-linked" is used herein to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for NHP will typically have its own operably-linked promoter sequence.

The nucleotide sequences encoding NHP used in the subject invention include "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological or serological activity as the native (naturally occurring) natriuretic peptide. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention. Homologous nucleotide and amino acid sequences include mammalian homologs of the human NHP sequences.

The NHP homologs include peptides containing, as a primary amino acid sequence, all or part of an exemplified NHP polypeptide sequence. The NHP homologs thus include NHP polypeptides having conservative substitutions, i.e., altered sequences in which functionally equivalent amino acid residues are substituted for residues within the sequence resulting in a peptide which is biologically active. For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 1). Conservative substitutions also include substitutions by amino acids having chemically modified side chains which do not eliminate the biological activity of the resulting NHP homolog.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman *Proc. Natl. Acad. Sci. USA*, 1988, 85(8):2444-2448; Altschul et al. *J. Mol. Biol.*, 1990, 215(3): 403-410; Thompson et al. *Nucleic Acids Res.*, 1994, 22(2): 4673-4680; Higgins et al. *Methods Enzymol.*, 1996, 266:383-402; Altschul et al. *J. Mol. Biol.*, 1990, 215(3):403-410; Altschul et al. *Nature Genetics*, 1993, 3:266-272).

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; York (1988); Biocomputing: Informatics and Genome Projects, Smith, D. W., ed., Academic Press, New York, 1993; York (1993); Computer Analysis of Sequence Data, Part 1, Griffin, A. M., and Griffin, H. G., eds., Humana Press, New Jersey, 1994; Jersey (1994); Sequence Analysis in Molecular Biology, von Heinje, G., Academic Press, 1987; Press (1987); Sequence Analysis Primer, Gribskov, M. and Devereux, J., eds., M. Stockton Press, New York, 1991; York (1991); and Carillo et al., *SIAM J. Applied Math.*, 48:1073 (1988).

The methods, pharmaceutical compositions, and vectors of the present invention can utilize biologically active fragments of nucleic acid sequences encoding the 126-amino acid atrial natriuretic factor (ANF) prohormone, such as nucleic acid sequences encoding $NHP_{1-30}$, $NHP_{31-67}$, $NHP_{79-98}$, $NHP_{99-126}$, and $NHP_{73-102}$, (SEQ ID NO: 1, SEQ ID NO:2, SEQ ID NO:3, SEQ ID NO:4, and SEQ ID NO:5, respectively), SEQ ID NO:6, and including biologically active fragments of the nucleic acid sequences encoding SEQ ID NO:1, SEQ ID NO:2, SEQ ID NO:3, SEQ ID NO:4, SEQ ID NO:5, and SEQ ID NO:6.

Representative fragments of the nucleotide sequences according to the invention will be understood to mean any polynucleotide fragment having at least 8 or 9 consecutive nucleotides, preferably at least 12 consecutive nucleotides, and still more preferably at least 15 or at least 20 consecutive nucleotides of the sequence from which it is derived. The upper limit for such fragments is one nucleotide less than the total number of nucleotides found in the full-length sequence (or, in certain embodiments, of the full length open reading frame (ORF) identified herein).

In other embodiments, fragments can comprise consecutive nucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, and up to one nucleotide less than the full length ANF prohormone. In some embodiments, fragments comprise biologically active fragments of SEQ ID NO:1, SEQ ID NO:2, SEQ ID NO:3, SEQ ID NO:4, SEQ ID NO:5, or SEQ ID NO:6.

It is also well known in the art that restriction enzymes can be used to obtain biologically active fragments of the nucleic acid sequences, such as those encoding SEQ ID NO:1, SEQ ID NO:2, SEQ ID NO:3, SEQ ID NO:4, SEQ ID NO:5, and SEQ ID NO:6. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512.

The methods and pharmaceutical compositions of the present invention can utilize amino acid sequences that are biologically active fragments of the 126-amino acid atrial natriuretic factor (ANF) prohormone, such as $NHP_{1-30}$, $NHP_{31-67}$, $NHP_{79-98}$, $NHP_{99-126}$, and $NHP_{73-102}$ (SEQ ID NO:1, SEQ ID NO:2, SEQ ID NO:3, SEQ ID NO:4, and SEQ ID NO:5, respectively), SEQ ID NO:6, and including biologically active fragments of SEQ ID NO:1, SEQ ID NO:2, SEQ ID NO:3, SEQ ID NO:4, SEQ ID NO:5, and SEQ ID NO:6.

Representative fragments of the polypeptides according to the invention will be understood to mean any polypeptide fragment having at least 8 or 9 consecutive amino acids, preferably at least 12 amino acids, and still more preferably at least 15 or at least 20 consecutive amino acids of the polypeptide sequence from which it is derived. The upper limit for such fragments is one amino acid less than the total number of amino acids found in the full-length sequence.

In other embodiments, fragments of the polypeptides can comprise consecutive amino acids of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, and up to one amino acid less than the full-length ANF prohormone. Fragments of polypeptides can be any portion of the full-length ANF prohormone amino acid sequence (including human or non-human mammalian homologs of the ANF prohormone) that exhibit biological activity, e.g., a C-terminally or N-terminally truncated version of the ANF prohormone, or an intervening portion of the ANF prohormone. In some embodiments, fragments comprise biologically active fragments of SEQ ID NO:1, SEQ ID NO:2, SEQ ID NO:3, SEQ ID NO:4, SEQ ID NO:5, and SEQ ID NO:6.

The present invention can be practiced using other biologically equivalent forms of ANF fragments or homologs thereof as can be appreciated by the sequence comparison below. Sequence similarities between mouse and human forms of ANP are shown where areas of conservation are clearly seen.

$Ca^{++}$ concentration (e.g., in epithelial cells), increased production of nitric oxide (NO), and decreased activation of NFkB.

The methods of the subject invention also contemplate the administration of cells that have been genetically modified to produce NHP, or biologically active fragments thereof. Such genetically modified cells can be administered alone or in combinations with different types of cells. Thus, genetically modified cells of the invention can be co-administered with other cells, which can include genetically modified cells or non-genetically modified cells. Genetically modified cells may serve to support the survival and function of the co-administered cells, for example.

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or

```
        NCBI BLAST Comparison of mouse (Query) to human (Sbjct)
                        ANP a.a. sequences.

Query:    1 MGSFSIT-LGFFLVLAFWLPGHIGANPVYSAVSNTDLMDFKNLLDHLEEKMPVEDEVMPP
            M SFS T + F L+LAF L G   ANP+Y+AVSN DLMDFKNLLDHLEEKMP+EDEV+PP
Sbjct:    1 MSSFSTTTVSFLLLLAFQLLGQTRANPMYNAVSNADLMDFKNLLDHLEEKMPLEDEVVPP Query:   60 QALSEQTEEAGAALSSLPEVPPWTGEVNPPLRDGSALGRSPWDPSDXXXXXXXXXXXXXX
            Q LSE  EEAGAALS LPEVPPWTGEV+P  RDG ALGR PWD SD
Sbjct:   61 QVLSEPNEEAGAALSPLPEVPPWTGEVSPAQRDGGALGRGPWDSSDRSALLKSKLRALLT Query:  120 GPRSLRRSSCFGGRIDRIGAQSGLGCNSFRY 150
              PRSLRRSSCFGGR+DRIGAQSGLGCNSFRY
Sbjct:  121 APRSLRRSSCFGGRMDRIGAQSGLGCNSFRY 151
```

The NHP of the invention can be prepared by well-known synthetic procedures. For example, the polypeptides can be prepared by the well-known Merrifield solid support method. See Merrifield (1963) *J. Amer. Chem. Soc.* 85:2149-2154 and Merrifield (1965) *Science* 150:178-185. This procedure, using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations since removal of the excess reagents at each step is effected simply by washing of the polymer.

Alternatively, these peptides can be prepared by use of well-known molecular biology procedures. Polynucleotides, such as DNA sequences, encoding the NHP of the invention can be readily synthesized. Such polynucleotides are a further aspect of the present invention. These polynucleotides can be used to genetically engineer eukaryotic or prokaryotic cells, for example, bacteria cells, insect cells, algae cells, plant cells, mammalian cells, yeast cells or fungi cells for synthesis of the peptides of the invention.

For purposes of the present invention, the biological activity attributable to the homologs and fragments of NHP and NHP-encoding nucleic acid sequences means the capability to prevent or alleviate symptoms associated with allergic disease, such as bronchoconstriction and inflammation. This biological activity can be mediated by one or more of the following mechanisms: increased production of intracellular naturally derived, and may contain genes, portions of genes, or other useful polynucleotides in addition to those encoding NHP. A translation initiation codon can be inserted as necessary, making methionine the first amino acid in the sequence. The term "genetic modification" is not intended to include naturally occurring alterations such as that which occurs through natural viral activity, natural genetic recombination, or the like. The genetic modification may confer the ability to produce NHP, wherein the cell did not previously have the capability, or the modification may increase the amount of NHP produced by the cell, e.g., through increased expression.

Exogenous nucleic acids and/or vectors encoding NHP can be introduced into a cell by viral vectors (retrovirus, modified herpes virus, herpes virus, adenovirus, adeno-associated virus, lentivirus, and the like) or direct DNA transfection (lipofection, chitosan-nanoparticle mediated transfection, calcium phosphate transfection, DEAE-dextran, electroporation, and the like), microinjection, cationic lipid-mediated transfection, transduction, scrape loading, ballistic introduction and infection (see, for example, Sambrook et al. [1989] *Molecular Cloning: A Laboratory Manual*, $2^{nd}$ Ed., Cold Spring Harbor Laboratory Press, Cold Spring Harbor, N.Y.).

Preferably, the exogenous nucleic acid sequence encoding NHP is operably linked to a promoter sequence that permits expression of the nucleic acid sequence in a desired tissue within the patient. The promoters can be inducible or tissue specific as necessary.

The genetically modified cell may be chosen from eukaryotic or prokaryotic systems, for example bacterial cells (Gram negative or Gram positive), yeast cells, animal cells, plant cells, and/or insect cells using baculovirus vectors. In some embodiments, the genetically modified cell for expression of the nucleic acid sequences encoding NHP, are human or non-human mammal cells.

According to the methods of the present invention, NHP or nucleic acid sequences encoding NHP can be administered to a patient in order to alleviate (e.g., reduce or eliminate) a variety of symptoms associated with allergic diseases, in various stages of pathological development, such as airway reactivity, airway inflammation, and airway remodeling. Treatment with NHP or nucleic acid sequences encoding NHP is intended to include prophylactic intervention to prevent onset of the symptoms associated with airway hyperreactivity, airway inflammation, and airway remodeling. The nucleic acid sequences and pharmaceutical compositions of the invention can be co-administered (concurrently or consecutively) to a patient with other therapeutic agents useful for treating airway reactivity, airway inflammation, and airway remodeling.

Expression vectors for NHP are any which are known in the art that will cause expression of NHP-encoding nucleic acid sequences in mammalian cells. Suitable promoters and other regulatory sequences can be selected as is desirable for a particular application. The promoters can be inducible or tissue specific as necessary. For example the cytomegalovirus (CMV) promoter (Boshart et al., Cell, 1985, 41:521-530) and SV40 promoter (Subramani et al., Mol. Cell. Biol., 1981, 1:854-864) have been found to be suitable, but others can be used as well. Optionally, the NHP-encoding nucleic acid sequences used in the subject invention include a sequence encoding a signal peptide upstream of the NHP-encoding sequence, thereby permitting secretion of the NHP from a host cell. Also, various promoters may be used to limit the expression of the peptide in specific cells or tissues, such as lung cells.

The pharmaceutical composition of the present invention can include a liposome component. According to the present invention, a liposome comprises a lipid composition that is capable of fusing with the plasma membrane of a cell, thereby allowing the liposome to deliver a nucleic acid molecule and/or a protein composition into a cell. Some preferred liposomes of the present invention include those liposomes commonly used in, for example, gene delivery methods known to those of skill in the art. Some preferred liposome delivery vehicles comprise multilamellar vesicle (MLV) lipids and extruded lipids, although the invention is not limited to such liposomes. Methods for preparation of MLV's are well known in the art. According to the present invention, "extruded lipids" are lipids which are prepared similarly to MLV lipids, but which are subsequently extruded through filters of decreasing size, as described in Templeton et al., Nature Biotech., 1997, 15:647-652, which is incorporated herein by reference in its entirety. Small unilamellar vesicle (SUV) lipids can also be used in the composition and method of the present invention. Other preferred liposome delivery vehicles comprise liposomes having a polycationic lipid composition (i.e., cationic liposomes). For example, cationic liposome compositions include, but are not limited to, any cationic liposome complexed with cholesterol, and without limitation, include DOTMA and cholesterol, DOTAP and cholesterol, DOTIM and cholesterol, and DDAB and cholesterol. Liposomes of the present invention can be any size, including from about 10 to 1000 nanometers (nm), or any size in between.

A liposome delivery vehicle of the present invention can be modified to target a particular site in a mammal, thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective immune activation at immunologically active organs can already be provided by the composition when the route of delivery is intravenous or intraperitoneal, without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., Biochemistry, 1986, 25: 5500-6; Ho et al., J Biol Chem, 1987a, 262: 13979-84; Ho et al., J Biol Chem, 1987b, 262: 13973-8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., FEBS Lett, 1987, 223: 42-6) or polyethylene glycol (PEG)-derived lipids (Klibanov et al., FEBS Lett, 1990, 268: 235-7), can be incorporated into the bilayer of a conventional liposome to form the so-called sterically-stabilized or "stealth" liposomes (Woodle et al., Biochim Biophys Acta, 1992, 1113: 171-99). Variations of such liposomes are described, for example, in U.S. Pat. No. 5,705,187 to Unger et al., U.S. Pat. No. 5,820, 873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

The NHP-encoding nucleic acid sequences of the present invention can be conjugated with chitosan. For example, DNA chitosan nanospheres can be generated, as described by Roy, K. et al. (1999, Nat Med 5:387). Chitosan allows increased bioavailability of the NHP-encoding nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue.

Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The term "patient" is intended to include such human and non-human mammalian species. According to the method of the present invention, human or non-human mammalian NHP (or nucleic acid sequences encoding human or non-human mammalian NHP) can be administered to the patient. The NHP may be naturally occurring within the patient's species or a different mammalian species. The expression vectors used in the subject invention can comprise nucleic acid sequences encoding any human or non-human mammalian NHP.

In another aspect, the present invention concerns pharmaceutical compositions containing a therapeutically effective amount of NHP, or nucleic acid sequences encoding NHP, and a pharmaceutically acceptable carrier. Preferably, the NHP-encoding nucleic acid sequences are contained within an expression vector, such as plasmid DNA or virus. The pharmaceutical composition can be adapted for administration to the airways of the patient, e.g., nose, sinus, throat and lung, for example, as nose drops, as nasal drops, by nebulization as an inhalant, vaporization, or other methods known in the art. Administration can be continuous or at distinct intervals as can be determined by a person skilled in the art.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, *Remington's Pharmaceutical Sciences* (Martin E W [1995] Easton Pa., Mack Publishing Company, 19$^{th}$ ed.) describes formulations that can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The NHP or nucleic acid sequences encoding NHP (and pharmaceutical compositions containing them) can be administered to a patient by any route that results in prevention or alleviation of symptoms associated with allergic disease, such as bronchoconstriction and/or inflammation. For example, the NHP or NHP-encoding nucleic acid molecule can be administered parenterally, intravenously (I.V.), intramuscularly (I.M.), subcutaneously (S.C.), intradermally (I.D.), orally, intranasally, etc. Examples of intranasal administration can be by means of a spray, drops, powder or gel and also described in U.S. Pat. No. 6,489,306, which is incorporated herein by reference in its entirety. One embodiment of the present invention is the administration of the invention as a nasal spray. Alternate embodiments include administration through any oral or mucosal routes, sublingual administration and even eye drops. However, other means of drug administrations are well within the scope of the present invention.

The NHP or NHP-encoding nucleic acid molecule is administered and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art. For example, an effect amount of NHP-encoding nucleic acid molecule is that amount necessary to provide a therapeutically effective amount of NHP, when expressed in vivo. The amount of NHP or NHP-encoding nucleic acid molecule must be effective to achieve improvement including but not limited to total prevention and to improved survival rate or more rapid recovery, or improvement or elimination of symptoms associated with allergen-induced airway hyper-reactivity and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

Standard molecular biology techniques known in the art and not specifically described were generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989) and in Perbal, A Practical Guide to Molecular Cloning, John Wiley & Sons, New York (1988), and in Watson et al., Recombinant DNA, Scientific American Books, New York and in Birren et al. (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659; and 5,272,057; and incorporated herein by reference. Polymerase chain reaction (PCR) was carried out generally as in PCR Protocols: A Guide To Methods And Applications, Academic Press, San Diego, Calif. (1990). In situ (In-cell) PCR in combination with Flow Cytometry can be used for detection of cells containing specific DNA and mRNA sequences (Testoni et al., *Blood*, 1996, 87:3822.)

The term "gene therapy", as used herein, refers to the transfer of genetic material (e.g., DNA or RNA) of interest into a host to treat or prevent a genetic or acquired disease or condition phenotype. The genetic material of interest encodes a product (e.g., a protein, polypeptide, peptide, or functional RNA) whose production in vivo is desired. For example, the genetic material of interest can encode a hormone, receptor, enzyme, polypeptide or peptide of therapeutic value. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy, cells are removed from a patient and, while being cultured, are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to produce the transfected gene product in situ.

In in vivo gene therapy, target cells are not removed from the subject, rather the gene to be transferred is introduced into the cells of the recipient organism in situ, that is within the recipient. Alternatively, if the host gene is defective, the gene is repaired in situ. These genetically altered cells have been shown to produce the transfected gene product in situ.

The gene expression vector is capable of delivery/transfer of heterologous nucleic acid sequences into a host cell. The expression vector may include elements to control targeting, expression and transcription of the nucleic acid sequence in a cell selective manner as is known in the art. It should be noted that often the 5'UTR and/or 3'UTR of the gene may be replaced by the 5'UTR and/or 3'UTR of the expression vehicle.

The expression vector can include a promoter for controlling transcription of the heterologous material and can be either a constitutive or inducible promoter to allow selective transcription. The expression vector can also include a selection gene.

Vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Aim Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and include, for example, stable or transient transfection, lipofection, electroporation, and infection with recombinant viral vectors.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of a DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

In another aspect, the present invention concerns an isolated peptide comprising the amino acid sequence $NHP_{73-102}$ (SEQ ID NO:5), or a biologically active fragment or homolog thereof. $NHP_{73-102}$ is amino acids 73-102 of the 151-amino acid long human atrial natriuretic factor (ANF)). In another aspect, the present invention concerns an isolated peptide comprising the amino acid sequence of SEQ ID NO:6, or a biologically active fragment or homolog thereof. SEQ ID NO:6 is a biologically active fragment of the human ANF. In another aspect, the present invention concerns an isolated nucleic acid molecule encoding the amino acid sequence of $NHP_{73-102}$ (SEQ ID NO:5), or a biologically active fragment or homolog thereof. In another aspect, the present invention concerns an isolated nucleic acid molecule (SEQ ID NO:13) encoding the amino acid sequence of SEQ ID NO:6, or a biologically active fragment or homolog thereof.

As used herein, the terms "peptide", "polypeptide", and "protein" refer to amino acid sequences of any length unless otherwise specified.

EXAMPLE 1

Expression of NHP in Human Type-II Alveolar A549 Cells and Murine Lung

A. Materials and Methods
Animals.

Six-week old female BALB/c mice from Jackson laboratory (Bar Harbor, Me.) were maintained in pathogen free conditions in accordance with animal research committee regulations.

Construction of NHP Expression Vector.

Total RNA was isolated from murine heart using Trizol reagent (LIFE TECHNOLOGY, Gaithersburg, Md.) following the manufacturer's protocol. The cDNA sequence for the 151 amino acid long pre-pro hormone ANF was amplified by RT-PCR. SEQ ID NO:13 was amplified using primers listed in SEQ ID NO:8 and SEQ ID NO:9. $NHP_{73-102}$ was amplified using primers listed in SEQ ID NO:10 and SEQ ID NO:11. A translation initiation codon was inserted in the forward primers (SEQ ID NO:8 and SEQ ID NO:10), so that the recombinant peptides had an additional amino acid, methionine, as the first amino acid apart from its known amino acid content. The PCR product was cloned in pVAX vector (INVITROGEN, Carlsbad, Calif.) at HindIII and XhoI sites. The cloned NHP$_{73-102}$ sequence was verified by DNA sequencing and its expression was checked in A549 human epithelial cells.

Estimation of NHP by EIA.

The expression of NHP was measured by utilizing a commercial kit (SPI-BIO, France) according to the manufacturer's instructions. The kit measures the rat NHP, which is homologous to the mouse NHP used in the present study.

B. Results

NHP was amplified using PCR and the product was cloned into pVAX vector, as described. Either pNHP$_{73-102}$ or empty plasmid vector pVAX were transfected to the human type-II alveolar cells (A549). To confirm the expression of NHP, cells and supernatants were collected 48 hours post-transfection and NHP concentrations were measured by ELISA. Cells transfected with pNHP produced NHP in both supernatant and cell extracts (FIG. 2A), whereas the cells transfected with pVAX did not. These results show that the NHP$_{73-102}$ peptide was expressed and secreted into the culture medium from the A549 cells.

EXAMPLE 2 pNHP Delivered with Lipofectin Intranasally Attenuates Airway Reactivity in Ovalbumin-Sensitized Mice A. Materials and Methods Animals.

Six-week old female BALB/c mice from Jackson laboratory (Bar Harbor, Me.) were maintained in pathogen free conditions in accordance with animal research committee regulations.

Allergen Sensitization, Intranasal Gene Transfer.

BALB/c mice (n=6) were sensitized once with intraperitoneal (i.p.) injection of 10 µg ovalbumin (OVA) precipitated with 1 mg of alum on day 1. Mice were intranasaly (i.n.) administered three times a day with either 25 µg/mouse pNHP$_{73-102}$ or vector control (pVAX) (10 µg of lipofectamine in PBS) on days 15, 18 and 21, as shown in FIG. 3A.

RT-PCR Analysis.

Total RNA was isolated from murine lung and spleen tissue using Trizol reagent (LIFE TECHNOLOGY, Gaithersburg, Md.) and RT-PCR was performed utilizing ANP specific primers as described before (Kumar M. et al., *Vaccine* 1999; 18:558-567). The resultant PCR products were analyzed by electrophoresis on a 1.5% agarose gel and the products visualized by staining with ethidium bromide.

Measurement of Ova Specific IgE.

Ova specific IgE was measured to monitor the degree of sensitization. Microtitre plates were coated overnight at 4° C. with 100 µl of OVA (5 µg/ml). Sera obtained at day 21 from sensitized and non-sensitized mice (n=4) were incubated to the antigen-coated wells and bound IgE was detected with biotinylated anti-mouse IgE (02112D; Pharmingen, Calif.). Biotin anti-mouse IgE (02122D) reacts specifically with the mouse IgE of Igh$^a$ and Igh$_b$ haplotypes and does not react with other IgG isotypes. Diluted streptavidin-peroxidase conjugate was added, the bound enzyme detected with TMB, and the absorbance read at 450 nm.

Pulmonary Function.

Airway hyperreactivity was measured in animals three days after the last intranasal DNA delivery following 24 hours of challenge with the ovalbumin (50 µg/mouse using a whole body plethysmograph (BUXCO, Troy, N.Y.), as previously described (Matsuse, H. et al., *J. Immunol.*, 2000, 164:6583-6592). Allergen-induced airway hyper-responsiveness (AHR) was measured on 10 days interval up to day 56. Mice were ova challenged 24 hours prior to each AHR measurement.

Statistical Analysis.

Pairs of groups were compared by the student's t-test. Differences between groups were considered significant at p<0.05. Values for all measurements are expressed as the mean±SD.

B. Results

The effect of pNHP gene transfer was examined in an ovalbumin-sensitized BALB/c mouse model. RT-PCR was performed to confirm the expression of ANP in murine lung and spleen. ANP specific transcript was observed in the lung tissue of mice receiving pANP construct and not from the mice receiving the empty plasmid vector (FIG. 1B). No expression of ANP was observed from the spleen tissue (data not shown).

Ovalbumin-specific IgE was measured in the serum to determine the degree of sensitization achieved following ovalbumin injection. Mice that received ovalbumin with alum had significantly (p<0.01) higher ovalbumin-specific IgE titers than the control group of mice that received PBS (FIG. 3C).

Figure 3D:
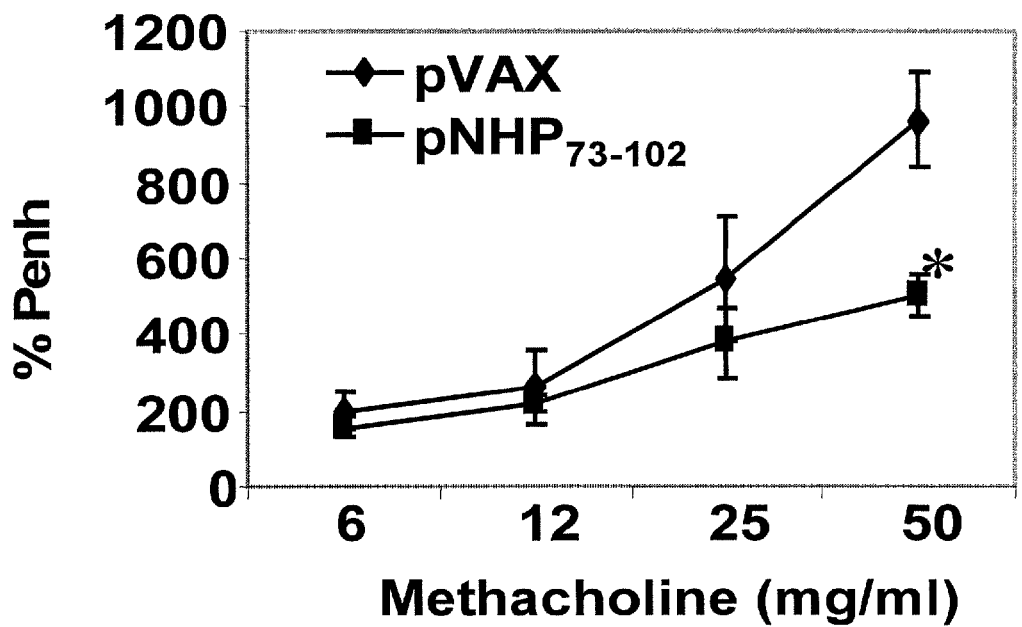
Figure 3E:
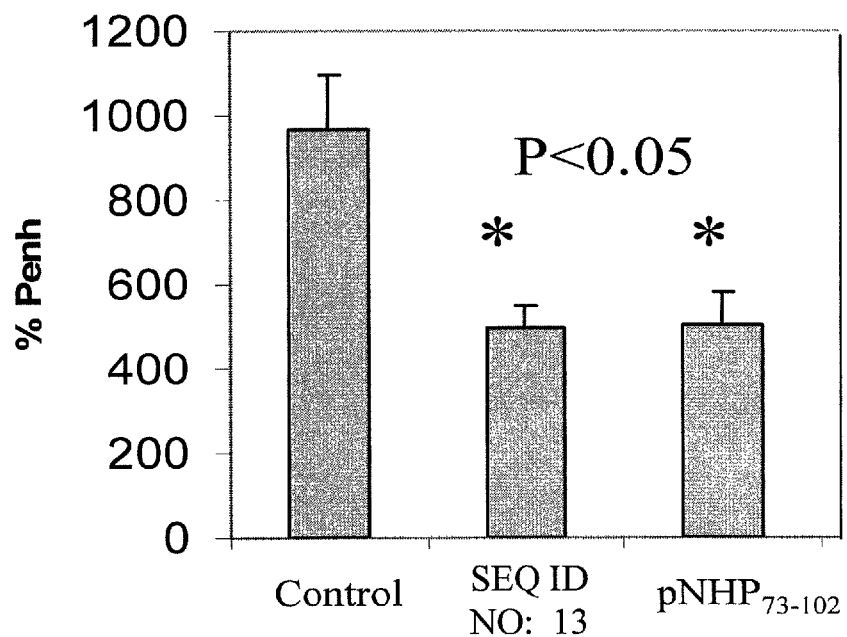

AHR was measured in BALB/c mice, sensitized with ovalbumin and administered with pNHP$_{73-102}$ or control vector plasmid prior to ovalbumin challenge. The control mice received empty vector. The experimental outline is shown in FIG. 3A. Mice administered pNHP showed significantly less AHR (p<0.05) than did controls to inhaled methacholine (FIG. 3D). Prophylactic treatment with either plasmid (SEQ ID NO:13) or pNHP$_{73-102}$ showed a reduction in % Penh suggesting that both plasmid are capable of prophylactically attenuating AHR.

Figure 4A:
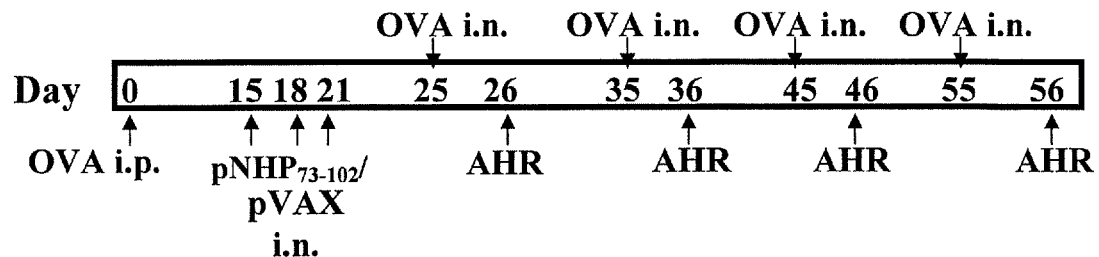
FIGS. 4A and 4B show the long-term effect on AHR following prophylaxis by $NHP_{73-102}$ gene transfer.
Figure 4B:
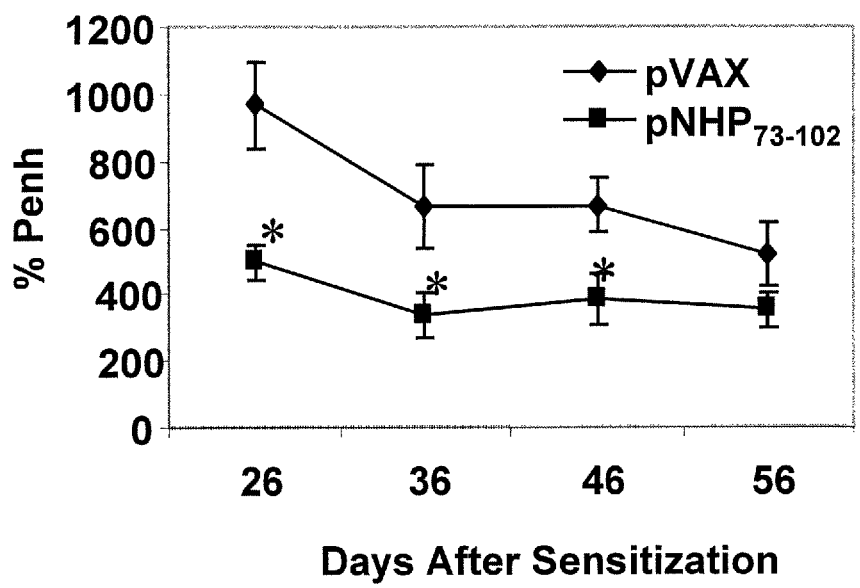

To determine the length of protection, following pNHP gene transfer mice were challenged at 10 d interval. The protection lasted for over a period of 25 days during which the AHR of pNHP treated mice was significantly lower (P<0.05) than the mice receiving control plasmid (FIGS. 4 A and B). Although there was a decrease in the AHR on day 56, the differences between values were not significant.

EXAMPLE 3

Chitosan-pNHP Nanoparticles Administered Intranasally Decrease Airway Hyper-Reactivity and Inflammation A. Materials and Methods Animals.

Female 6 to 8 week-old wild type BALB/c mice from Jackson Laboratory (Bar Harbor, Me.) were maintained in pathogen-free conditions at the University of South Florida College of Medicine vivarium. All procedures were reviewed and approved by the committees on animal research at the University of South Florida College of Medicine and VA Hospital.

Preparation of Chitosan-pNHP Nanoparticles.

pNHP$_{73-102}$ encoding DNA was cloned in the mammalian expression vector pVAX (INVITROGEN, San Diego, Calif.), and complexed with chitosan, as described previously (Hulks, G. et al., *Clin Sci,* 1990, 79:51-55; Angus, R. M. et al., *Clin Exp Allergy,* 1994, 24:784-788). Briefly, recombinant plasmid dissolved in 25 mM Na$_2$SO$_4$ was heated for 10 min at 55° C. Chitosan (VANSON, Redmond, Wash.) was dissolved in 25 mM Na acetate, pH 5.4, to a final concentration of 0.02% and heated for 10 min at 55° C. After heating, chitosan and DNA were mixed, vortexed vigorously for 20-30 seconds, and stored at room temperature until use.

Reversal of Established AHR.

Mice were sensitized i.p. with 50 μg OVA/alum on day 1 followed by intranasal challenge with 50 μg of OVA on day 14. On days 21-23, mice were given 25 μg of pNHP/chitosan i.n. per mouse. Mice were further challenged i.n. with OVA (50 μg/mouse) on days 27 through 29 and AHR was measured on day 30. Mice were bled and sacrificed on day 31, and spleens and lungs were removed.

Examination of Bronchoalveolar Ravage Fluid (BALF).

Mice were sacrificed and lungs were lavaged with 1 ml of PBS introduced through the trachea. The BALF was centrifuged 10 min. at 300×g and cells were rinsed with PBS and resuspended. Aliquots of the cell suspension were applied to slides using a CYTOSPIN apparatus (SHANDON SOUTHERN), stained and examined microscopically. Cells were identified as monocytes, eosinophils, neutrophils, and lymphocytes by morphological characteristics. Two slides per mouse (n=4) were counted by three blinded investigators.

Statistical Analysis.

Pairs of groups were compared by the student's t-test. Differences between groups were considered significant at p<0.05. Values for all measurements are expressed as the mean±SD.

B. Results

Figure 5A:
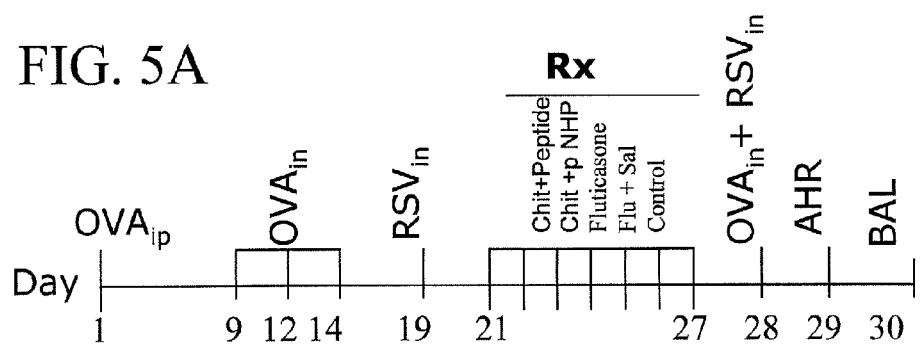
FIGS. 5A-5C show that administration of chitosan-pNHP nanoparticles exhibit a therapeutic effect for allergen-RSV induced asthma and reversal of asthma in mice.
Figure 5B:
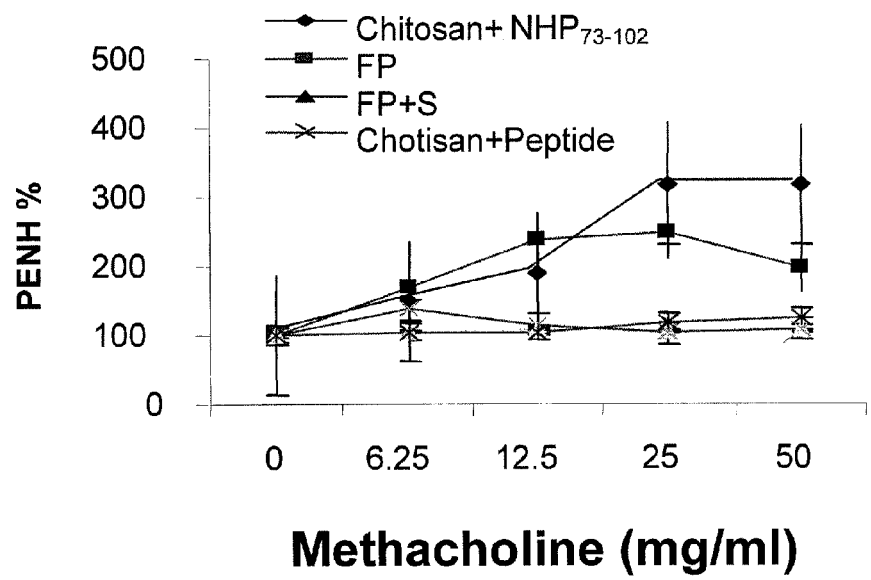
Figure 5C:
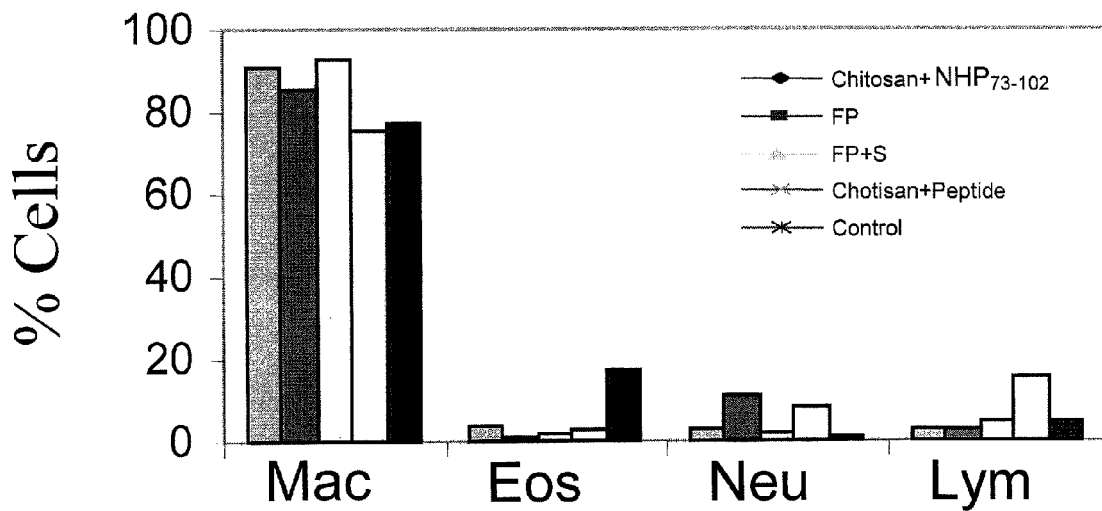
Figure 7A:
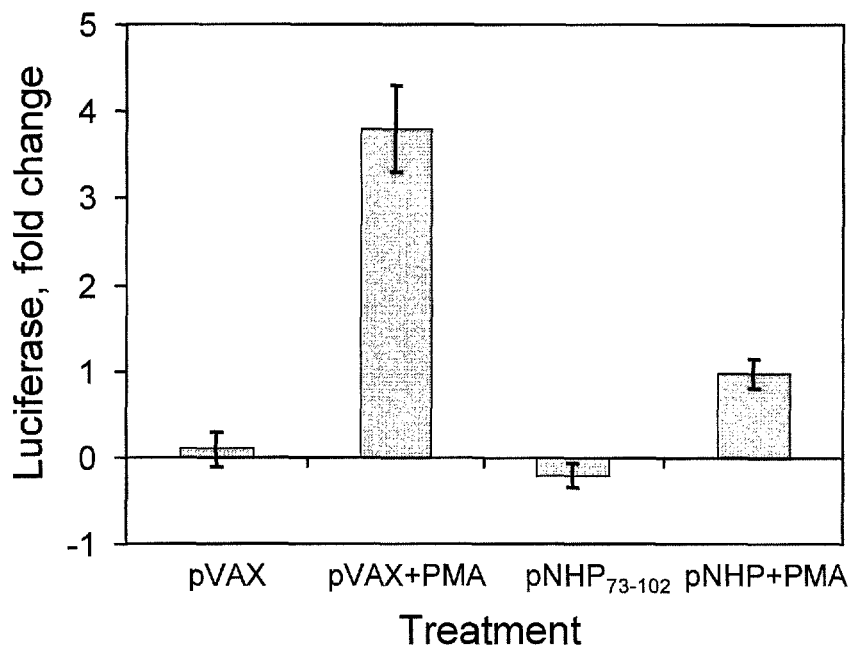
FIGS. 7A and 7B show that $pNHP_{73-102}$ exerts its anti-inflammatory activity in the lung by decreasing NFκB activation in epithelial cells. A549 (FIG. 7A) or NHBE (FIG. 7B) cells were co-transfected with $pNHP_{73-102}$ or vector pVAX (pV) alone, NFκB plasmid carrying the luciferase reporter gene (pNFκB-luc reporter plasmid) (MERCURY PROFILING SYSTEM, CLONTECH), and pLacZ normalization control. NFκB was activated 24 hr after transfection by incubating cells with 20 ng/ml phorbol myristoyl acetate (PMA) (for A549 cells) or 10 ng/ml of TNF-α (for NHBE cells). Luciferase activity was detected using the DUAL LUCIFERASE REPORTER Assay kit (CLONTECH) and DYNEX MLX luminometer. Data (average of three readings+SEM) are expressed as fold change in luciferase activity in arbitrary units relative to vector control.
Figure 7B:
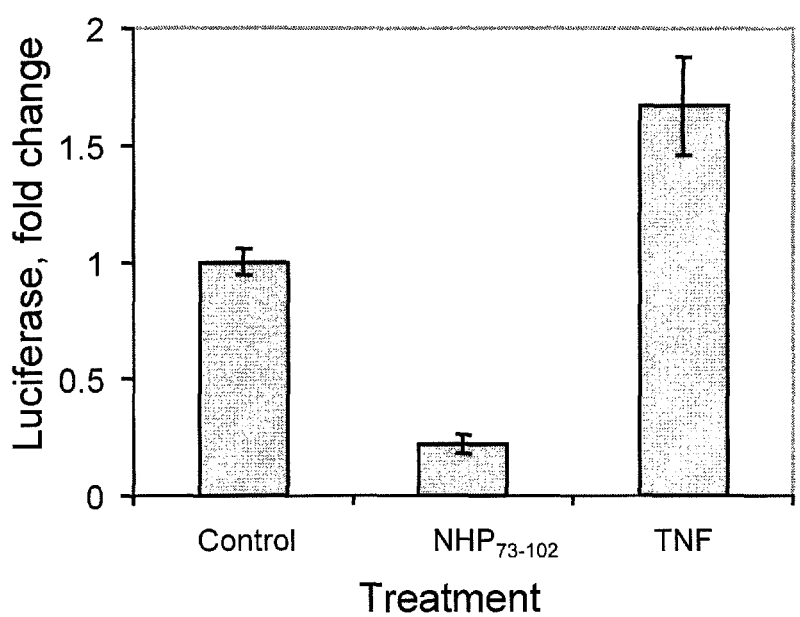

A combination of allergen exposure and respiratory syncytial virus induces chronic asthma phenotype in BAALB/c mice. To determine whether therapeutic administration of chitosan-pNHP can attenuate established asthma induced by allergen exposure and RSV infection, mice were first sensitized and challenged with OVA and then infected with RSV and subsequently given Chitosan+pNHP (CHIpP) therapy, as shown in the protocol of FIG. 5A. Airway hyper-reactivity (% Penh) was measured by whole body plethysmography (FIG. 5B). The results show a complete reversal to the basal level of AHR in the group of mice that were treated with CHIpP. To determine whether CHIpP therapy decreases established pulmonary inflammation, lungs of treated and then OVA-challenged mice were lavaged and BAL cells were examined. The number of eosinophils in the BAL fluid showed a significant reduction in the CHIpP-treated mice compared with the untreated control group, as shown in FIG. 5C.

EXAMPLE 4 pNHP Induces Production of Nitric Oxide by Activating Constitutive Nitric Oxide Synthase in Human in Lung Epithelial Cells A. Materials and Methods Cell Lines and Culture Conditions.

The human alveolar type II epithelial cell line A549 (ATCC) was cultured at 37° C. in Dulbecco's modified Eagle's medium containing 10% fetal bovine serum and 100 U/ml each of penicillin and streptomycin in an atmosphere of 5% $CO_2$/95% air. Cells were subcultured weekly and used between passages 9 and 22. Experiments were repeated with primary NHBE obtained from CLONETICS (Walkersville, Md.) from pooled donors. These cells were cultured in BEBM medium supplied by the vendor and supplemented with 10% fetal bovine serum and a mix of growth factors without antibiotics. Cells were grown at 37° C. in 5% $CO_2$/95% and used between passages 3 and 9.

Expression Plasmids and Transfection.

The construction of plasmid encoding $NHP_{73-102}$ has been described previously (Kumar, M et al., *J Allergy Clin Immunol.*, 2002, 110:879-82). For transfection of epithelial cells, cells at 60% confluence (log phase) were transfected 4 hr at 37° C. with plasmid DNA (1 μg per $10^6$ cells) complexed with lipofectamine (GIBCOBRL Life Technologies). Complete medium was then added to the cultures and the cells were incubated at 37° C. for 24 to 48 h to allow expression of the natriuretic peptides.

Assay for Nitric Oxide.

The assay for nitric oxide (NO) is based on that of Misko et al. (Misko, T P et al., *Anal Biochem.*, 1993, 214:11-6) and measures nitrite, the stable breakdown product of NO, which is reacted with diaminonaphthalene to produce a fluorescent compound. A549 or NHBE cells were transfected with plasmid/lipofectamine complexes as described above. At specific time points, 100 μl samples of culture medium were removed and stored at −20° C. After all samples were taken, they were cleared by centrifugation and 10 μl of a freshly prepared solution of 0.02 mg/ml diaminonaphthalene was added to each tube, shaken, and allowed to react for 10 min at room temperature. The reaction was stopped by addition of 30 μl of 0.5 M NaOH and the fluorescence of the samples was read using a quartz microcuvet (3 mm path length) in a JASCO spectrofluorometer with excitation at 365 nm and emission at 409 nm. Nitrite standards were run in the same medium as the experimental samples to generate a standard curve which was used to calibrate the readings. As a positive control, one set of wells was incubated with 1 μM calcium ionophore, A23187 (SIGMA).

B. Results

NO is a bronchodilator and $Ca^{++}$-calmodulin binding activates the constitutive form of nitric oxide synthase (cNOS) in epithelial cells (Howarth, P. H. et al., *Int Arch Allergy Immunol.*, 1995, 107:228-30). To determine whether the increased intracellular $Ca^{++}$ seen in $NHP_{73-102}$-transfected cells affects nitric oxide (NO) levels, aliquots of the medium were removed before the $Ca^{++}$ assay and mixed with diaminonaphthalene which reacts with nitrite (from the reaction of NO and water) to produce a fluorescent compound. NO generation was significantly higher in cells expressing $NHP_{73-102}$ (FIGS. 3A and B). To verify that NO production was due to the constitutive NOS, one aliquot of cells was incubated during the expression phase with 1 mM $N_\omega$-nitro-L-arginine methyl ester, an arginine analog that blocks cNOS production of NO. The enhanced NO generation was inhibited by pretreatment of the cells with N-nitro-L-arginine methyl ester, which blocks cNOS activity (FIG. 3C). Airway smooth muscle hypertrophy and hyperplasia are important determinants of airway remodeling and bronchial responsiveness in asthma. $NHP_{73-102}$ appears to act on epithelial cells to produce NO via constitutive NOS, which in turn controls bronchial hyperreactivity and proliferation of airway smooth muscle cells.

EXAMPLE 5 pNHP Induces Anti-Inflammatory Response in the Lung by Decreasing NfkB Activation of Epithelial Cells A. Materials and Methods Luciferase Reporter Assay for NFκB Activation.

A549 and NHBE cells were grown to about 60% confluence in 12-well culture plates and transfected using LIPOFECTAMINE 2000 (INVITROGEN, Carlsbad Calif.). Cells were transfected with a luciferase construct under the control of an NFκB-activatable promoter (MERCURY PROFILING SYSTEM, CLONTECH, Palo Alto Calif.) and pLacZ as a normalization control either with or without pANP. Relative amounts of plasmid DNA and lipofectamine reagent were optimized for NHBE cells and cells were transfected for 4 h in serum-free DMEM without antibiotics at 37° C. After transfection, DMEM with 10% FBS was added and cells were incubated for 24 to 48 h at 37° C. Cells were harvested at specific time points and lysates were assayed for luciferase activity using the DUAL LUCIFERASE Assay System (PROMEGA, Madison Wis.) read in an MLX microplate luminometer (DYNEX TECHNOLOGIES, Chantilly Va.). Transfection efficiencies were normalized by measuring β-galactosidase activity.

Statistical Analysis.

Experiments were repeated a minimum of three times and data are expressed as means±SEM. Pairs of groups were compared through the use of Student's t tests. Differences between groups were considered significant at $p \leq 0.05$.

B. Results

To study the potential role of NHP in regulating inflammation, A549 cells were transfected with pNHP plasmid encoding amino acids 73-102 ($pNHP_{73-102}$) and the activation of NFκB, which controls a number of genes encoding proinflammatory molecules and is key to the inflammatory cascade and has been linked to inflammation, was examined (Ishii, Y. et al., *J Anat.*, 1989, 166:85-95; Boiteau, R. et al., *Am Rev Res Dis.*, 1988, 137:A484). The results showed that cells cotransfected with pNHP significantly decreased luciferase activity compared to control plasmid suggesting that pNHP is capable of inhibiting PMA-induced NFκB activation in A549 cells and in NHBE cells, as shown in FIGS. 6A-6B. These results indicate that pNHP possesses potential anti-inflammatory activities, and that it may exert its bronchodilatory effect by stimulating the production of NO and its anti-inflammatory effect by deactivating NFκB, the central molecule controlling inflammation in asthmatic airways.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of treating a respiratory allergic disease in a mammal having the disease, comprising administering a plasmid DNA vector to an airway of the mammal, wherein the plasmid DNA vector comprises a nucleic acid sequence encoding a natriuretic hormone peptide (NHP), and an operably-linked promoter sequence, and wherein the NHP is expressed and alleviates at least one symptom of the disease.

2. The method of claim 1, wherein the NHP comprises an amino acid sequence selected from the group consisting of SEQ ID NO: 1, SEQ ID NO:2, SEQ ID NO:3, SEQ ID NO:4, SEQ ID NO:5 and SEQ ID NO:6, or a biologically active fragment or homolog of any of the foregoing.

3. The method of claim 1, wherein the plasmid DNA vector is administered with a pharmaceutically acceptable carrier.

4. The method of claim 1, wherein the plasmid DNA vector is administered with chitosan.

5. The method of claim 1, wherein the NHP causes a bronchodilatory effect in the mammal.

6. The method of claim 1, wherein the NHP inhibits airway reactivity, airway inflammation, or airway remodeling in the mammal.

7. The method of claim 1, wherein the mammal is human.

8. The method of claim 1, wherein the respiratory allergic disease is asthma.

9. The method of claim 1, wherein the mammal has airway hyper-reactivity (AHR) and the NHP reduces the AHR.

10. The method of claim 1, wherein the mammal has pulmonary inflammation, and the NHP reduces the inflammation.

11. The method of claim 1, wherein the respiratory allergic disease is allergen-induced asthma.

12. The method of claim 1, wherein the respiratory allergic disease is respiratory syncytial virus (RSV)-induced asthma.

13. The method of claim 7, wherein the human is suffering from asthma.

14. The method of claim 7, wherein the human has airway hyper-reactivity (AHR) and the NHP reduces the AHR.

15. The method of claim 7, wherein the human has pulmonary inflammation, and the NHP reduces the inflammation.

16. The method of claim 7, wherein the respiratory allergic disease is allergen-induced asthma.

17. The method of claim 7, wherein the respiratory allergic disease is respiratory syncytial virus (RSV)-induced asthma.

18. The method of claim 1, wherein the NHP comprises an amino acid sequence comprising SEQ ID NO:5.

19. The method of claim 1, wherein the NHP comprises an amino acid sequence comprising SEQ ID NO:6.

20. The method of claim 1, wherein the plasmid DNA vector is administered orally or intranasally.

21. The method of claim 4, wherein the plasmid DNA vector is conjugated with the chitosan.

22. The method of claim 1, wherein the NHP comprises an amino acid sequence comprising SEQ ID NO:5 or a homolog of SEQ ID NO:5 having at least one conservative amino acid substitution.

23. The method of claim 1, wherein the NHP consists of the amino acid sequence of SEQ ID NO:6.

24. The method of claim 1, wherein the NHP increases production of nitric oxide in airway epithelial cells of the mammal.

* * * * *

UNITED STATES PATENT AND TRADEMARK OFFICE
CERTIFICATE OF CORRECTION

PATENT NO. : 8,623,835 B2  
APPLICATION NO. : 11/936491  
DATED : January 7, 2014  
INVENTOR(S) : Shyam S. Mohapatra Page 1 of 1

It is certified that error appears in the above-identified patent and that said Letters Patent is hereby corrected as shown below:

In the Specification

Column 5,  
Lines 20-23, "(ANP) or $^{99}$SLRRSSC" should read --(ANP) or NHP$_{99-126}$:$^{99}$SLRRSSC--

Column 9,  
Line 63, "aga tet gcc" should read --aga tct gcc--  
Line 65, "agc eta cga" should read --agc cta cga--

Column 23,  
Line 57, "Igh$^a$ and Igh$_b$" should read --Igh$^a$ and Igh$^b$--

Column 25,  
Line 11, "Ravage Fluid" should read --lavage fluid--

Column 26,  
Line 56, "NtkB Activation" should read --NFkB Activation--

Signed and Sealed this  
Seventeenth Day of June, 2014

Michelle K. Lee  
*Deputy Director of the United States Patent and Trademark Office*

SEQUENCE LISTING

```
<160> NUMBER OF SEQ ID NOS: 19

<210> SEQ ID NO 1
<211> LENGTH: 30
<212> TYPE: PRT
<213> ORGANISM: Homo sapiens

<400> SEQUENCE: 1

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp
            20                  25                  30

<210> SEQ ID NO 2
<211> LENGTH: 37
<212> TYPE: PRT
<213> ORGANISM: Homo sapiens

<400> SEQUENCE: 2

Glu Val Val Pro Pro Gln Val Leu Ser Glu Pro Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 3
<211> LENGTH: 20
<212> TYPE: PRT
<213> ORGANISM: Homo sapiens

<400> SEQUENCE: 3

Ser Ser Asp Arg Ser Ala Leu Leu Lys Ser Lys Leu Arg Ala Leu Leu
1               5                   10                  15

Thr Ala Pro Arg
            20

<210> SEQ ID NO 4
<211> LENGTH: 28
```

```
<212> TYPE: PRT
<213> ORGANISM: Homo sapiens

<400> SEQUENCE: 4

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 5
<211> LENGTH: 30
<212> TYPE: PRT
<213> ORGANISM: Mus musculus

<400> SEQUENCE: 5

Gly Ser Pro Trp Asp Pro Ser Asp Arg Ser Ala Leu Leu Lys Ser Lys
1               5                   10                  15

Leu Arg Ala Leu Leu Ala Gly Pro Arg Ser Leu Arg Arg Ser
            20                  25                  30

<210> SEQ ID NO 6
<211> LENGTH: 37
<212> TYPE: PRT
<213> ORGANISM: Mus musculus

<400> SEQUENCE: 6

Val Ser Asn Thr Asp Leu Met Asp Phe Lys Asn Leu Leu Asp His Leu
1               5                   10                  15

Glu Glu Lys Met Pro Val Glu Asp Glu Val Met Pro Pro Gln Ala Leu
            20                  25                  30

Ser Glu Gln Thr Glu
        35

<210> SEQ ID NO 7
<211> LENGTH: 151
<212> TYPE: PRT
<213> ORGANISM: Homo sapiens

<400> SEQUENCE: 7

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150
```

```
<210> SEQ ID NO 8
<211> LENGTH: 35
<212> TYPE: DNA
<213> ORGANISM: Mus musculus

<400> SEQUENCE: 8
gacggcaagc ttactatggg cagcccctgg gaccc                              35

<210> SEQ ID NO 9
<211> LENGTH: 33
<212> TYPE: DNA
<213> ORGANISM: Mus musculus

<400> SEQUENCE: 9 accccccctcg agttattatc ttcgtaggct ccg                               33

<210> SEQ ID NO 10
<211> LENGTH: 33
<212> TYPE: DNA
<213> ORGANISM: Mus musculus

<400> SEQUENCE: 10
aatcctaagc ttagtatggt gtccaacaca gat                                33

<210> SEQ ID NO 11
<211> LENGTH: 41
<212> TYPE: DNA
<213> ORGANISM: Mus musculus

<400> SEQUENCE: 11
tgcgaactcg agttactcag tctgctcact cagggcctgc g                       41

<210> SEQ ID NO 12
<211> LENGTH: 93
<212> TYPE: DNA
<213> ORGANISM: Mus musculus

<400> SEQUENCE: 12
atgggcagcc cctgggaccc ctccgataga tctgccctct tgaaaagcaa actgagggct   60
ctgctcgctg gccctcggag cctacgaaga taa                                93

<210> SEQ ID NO 13
<211> LENGTH: 117
<212> TYPE: DNA
<213> ORGANISM: Mus musculus

<400> SEQUENCE: 13
atggtgtcca acacagatct gatggatttc aagaacctgc tagaccacct ggaggagaag   60
atgccggtag aagatgaggt catgcccccg caggccctga gtgagcagac tgagtaa      117

<210> SEQ ID NO 14
<211> LENGTH: 845
<212> TYPE: DNA
<213> ORGANISM: Homo sapiens

<400> SEQUENCE: 14
tggcgaggga cagacgtagg ccaagagagg ggaaccagag aggaaccaga ggggagagac   60
agagcagcaa gcagtggatt gctccttgac gacgccagca tgagctcctt ctccaccacc   120
accgtgagct tcctccttttt actggcattc cagctcctag gtcagaccag agctaatccc   180
atgtacaatg ccgtgtccaa cgcagacctg atggatttca gaatttgct ggaccatttg   240
```

```
gaagaaaaga tgcctttaga agatgaggtc gtgcccccac aagtgctcag tgagccgaat      300
gaagaagcgg gggctgctct cagcccctc cctgaggtgc ctccctggac cggggaagtc       360
agcccagccc agagagatgg aggtgccctc gggcggggcc cctgggactc ctctgatcga      420
tctgccctcc taaaaagcaa gctgagggcg ctgctcactg cccctcggag cctgcggaga      480
tccagctgct tcggggcag  gatggacagg attggagccc agagcggact gggctgtaac      540
agcttccggt actgaagata acagccaggg aggacaagca gggctgggcc tagggacaga      600
ctgcaagagg ctcctgtccc ctggggtctc tgctgcattt tgtgtcatctt gttgccatgg     660 agttgtgatc atcccatcta agctgcagct tcctgtcaac acttctcaca tcttatgcta      720
actgtagata aagtggtttg atggtgactt cctcgcctct cccacccat gcattaaatt       780 ttaaggtaga acctcacctg ttactgaaag tggtttgaaa gtgaataaac ttcagcacca      840
tggac                                                                  845

<210> SEQ ID NO 15
<211> LENGTH: 2583
<212> TYPE: DNA
<213> ORGANISM: Homo sapiens

<400> SEQUENCE: 15
ggatccattt gtctcgggct gctggctgcc tgccatttcc tcctctccac ccttatttgg       60
aggccctgac agctgagcca caaacaaacc aggggagctg ggcaccagca agcgtcaccc      120 tctgttttccc cgcacggtac cagcgtcgag agaaagaat cctgaggcac ggcggtgaga       180
taaccaagga ctcttttta ctcttctcac acctttgaag tgggagcctc ttgagtcaaa       240
tcagtaagaa tgcggctctt gcagctgagg gtctggggg ctgttggggc tgcccaaggc      300 agagagggc tgtgacaagc cctgcggatg ataactttaa aagggcatct cctgctggct       360
tctcacttgg cagctttatc actgcaagtg acagaatggg gagggttctg tctctcctgc      420
gtgcttggag agctgggggg ctataaaaag aggcggcact gggcagctgg agacagggga     480
cagacgtagg ccaagagagg ggaaccagag aggaaccaga ggggagagac agagcagcaa      540
gcagtggatt gctccttgac gacgccagca tgagctcctt ctccaccacc accgtgagct      600
tcctcctttt actggcattc cagctcctag gtcagaccag agctaatccc atgtacaatg      660
ccgtgtccaa cgcagacctg atggatttca aggtagggcc aggaaagcgg gtgcagtctg      720
gggccagggg gctttctgat gctgtgctca ctcctcttga tttcctccaa gtcagtgagg      780
tttatccctt tccctgtatt ttccttttct aaagaatttg ctggaccatt tggaagaaaa      840
gatgccttta gaagatgagg tcgtgccccc acaagtgctc agtgagccga atgaagaagc      900
gggggctgct ctcagccccc tccctgaggt gcctccctgg accggggaag tcagcccagc      960
ccagagagat ggaggtgccc tcgggcgggg cccctgggac tcctctgatc gatctgccct     1020
cctaaaaagc aagctgaggg cgctgctcac tgcccctcgg agcctgcgga gatccagctg     1080 cttcggggc aggatggaca ggattggagc ccagagcgga ctgggctgta acagcttccg     1140
ggtaagagga ctggggatg gaaatgggat gggatggaca ctactgggag acaccttcag     1200
caggaaaggg accaatgcag aagctcattc cctctcaagt ttctgcccca acacccagag     1260
tgccccatgg gtgtcaggac atgccatcta ttgtccttag ctagtctgct gagaaaatgc     1320
ttaaaaaaaa aagggggggg gctgggcacg gtcgtcacgc ctgtaatccc agcactttgg     1380
gaggccaggc agcggatcat gaggtcaaga gatcaagact atcctggcca acatggtgaa     1440
accccagctc tactaaaaat acaaaaatta gctgggtgtg tggcgggcac ctgtactctc     1500
```

```
agctacttgg gaggctgagg caggagaatc acttgaaccc aggaggcaga ggttgcagtg   1560
agcagagatc acgccactgc agtccagcct aggtgataga gcgagactgt ctcaaaaaaa   1620
aaaaaaaaag gccaggcgcg gtggctcacg cctgtaatcc cagcgctttg ggaggccaag   1680
gcgggtggat cacgaggtca ggagatggag accatcctgg ctaacacggt gaaacccccgt   1740 ctctactaaa aatacaaaaa attagccagg cgtggtggca ggcgcctgta agtcctagct   1800
actccggagg ctgaggcagg agaatggcgt gaacccggga ggcggagctt gcagtgagca   1860
gagatggcac cactgcactc cagcctgggc gacagagcaa gactccgtct caaaaaaaa   1920 aaaaaaaaaa gcaactgcca ctagcactgg gaaattaaaa tattcataga gccaagttat   1980
ctttgcatgg ctgattagca gttcatattc ctccccagaa ttgcaagatc ctgaagggct   2040
taagtgaaat ttactctgat gagtaacttg cttatcaatt catgaagctc agagggtcat   2100
caggctgggg tgggggccgg tgggaagcag gtggtcagta atcaagttca gaggatgggc   2160
acactcatac atgaagctga cttttccagg acagccaggt caccaagcca gatatgtctg   2220
tgttctcttt gcagtactga agataacagc cagggaggac aagcagggct gggcctaggg   2280
acagactgca agaggctcct gtcccctggg gtctctgctg catttgtgtc atcttgttgc   2340
catggagttg tgatcatccc atctaagctg cagcttcctg tcaacacttc tcacatctta   2400
tgctaactgt agataaagtg gtttgatggt gacttcctcg cctctcccac cccatgcatt   2460 aaatttaag gtagaacctc acctgttact gaaagtggtt tgaaagtgaa taaacttcag   2520
caccatggac agaagacaaa tgcctgcgtt ggtgtgcttt ctttcttctt gggaagagaa   2580
ttc                                                                 2583
```

<210> SEQ ID NO 16
<211> LENGTH: 152
<212> TYPE: PRT
<213> ORGANISM: Mus musculus

<400> SEQUENCE: 16

```
Met Gly Ser Phe Ser Ile Thr Leu Gly Phe Phe Leu Val Leu Ala Phe
1               5                   10                  15

Trp Leu Pro Gly His Ile Gly Ala Asn Pro Val Tyr Ser Ala Val Ser
                20                  25                  30

Asn Thr Asp Leu Met Asp Phe Lys Asn Leu Leu Asp His Leu Glu Glu
            35                  40                  45

Lys Met Pro Val Glu Asp Glu Val Met Pro Gln Ala Leu Ser Glu
        50                  55                  60

Gln Thr Glu Glu Ala Gly Ala Ala Leu Ser Ser Leu Pro Glu Val Pro
65                  70                  75                  80

Pro Trp Thr Gly Glu Val Asn Pro Pro Leu Arg Asp Gly Ser Ala Leu
                85                  90                  95

Gly Arg Ser Pro Trp Asp Pro Ser Asp Arg Ser Ala Leu Leu Lys Ser
                100                 105                 110

Lys Leu Arg Ala Leu Leu Ala Gly Pro Arg Ser Leu Arg Arg Ser Ser
            115                 120                 125

Cys Phe Gly Gly Arg Ile Asp Arg Ile Gly Ala Gln Ser Gly Leu Gly
        130                 135                 140

Cys Asn Ser Phe Arg Tyr Arg Arg
145                 150
```

<210> SEQ ID NO 17
<211> LENGTH: 878
<212> TYPE: DNA

```
<213> ORGANISM: Mus musculus

<400> SEQUENCE: 17
caaaagctga gagagagaga gaaagaaacc agagtgggca gagacagcaa acatcagatc      60
gtgccccgac ccacgccagc atgggctcct tctccatcac cctgggcttc ttcctcgtct     120
tggccttttg gcttccaggc catattggag caaatcctgt gtacagtgcg gtgtccaaca     180
cagatctgat ggatttcaag aacctgctag accacctgga ggagaagatg ccggtagaag     240
atgaggtcat gccccgcag gccctgagtg agcagactga ggaagcaggg gccgcactta     300
gctccctccc cgaggtgcct ccctggactg gggaggtcaa cccacctctg agagacggca     360
gtgctctagg gcgcagcccc tgggacccct ccgatagatc tgccctcttg aaaagcaaac     420
tgagggctct gctcgctggc cctcggagcc tacgaagatc cagctgcttc gggggtagga     480
ttgacaggat tggagcccag agtggactag gctgcaacag cttccggtac cgaagataac     540
agccaaggag gaaaaggcag tcgattctgc ttgagcagat cgcaaaagat cctaagccct     600
tgtggtgtgt cacgcagctt ggtcacattg ccactgtggc gtggtgaaca ccctcctgga     660
gctgcggctt cctgccttca tctatcacga tcgatgttaa atgtagatga gtggtctagt     720
ggggtcttgc ctctcccact ctgcatatta aggtagatcc tcacccttt cagaaagcag     780 ttggaaaaaa aaaaaaagaa taaacttcag caccaaggac agacgccgag gccctgatgt     840
gcttctttgg cttctgccct cagttctttg ctctcccc                             878

<210> SEQ ID NO 18
<211> LENGTH: 90
<212> TYPE: DNA
<213> ORGANISM: Mus musculus

<400> SEQUENCE: 18
ggcagcccct gggacccctc cgatagatct gccctcttga aaagcaaact gagggctctg      60
ctcgctggcc ctcggagcct acgaagatcc                                      90

<210> SEQ ID NO 19
<211> LENGTH: 111
<212> TYPE: DNA
<213> ORGANISM: Mus musculus

<400> SEQUENCE: 19
gtgtccaaca cagatctgat ggatttcaag aacctgctag accacctgga ggagaagatg      60
ccggtagaag atgaggtcat gccccgcag gccctgagtg agcagactga g               111
```